US008609065B2

(12) United States Patent
Kuik-Romeijn et al.

(10) Patent No.: US 8,609,065 B2
(45) Date of Patent: Dec. 17, 2013

(54) MOLECULES FOR TARGETING COMPOUNDS TO VARIOUS SELECTED ORGANS, TISSUES OR TUMOR CELLS

(75) Inventors: Petra Van Kuik-Romeijn, Utrecht (NL); Gerard Johannes Platenburg, Voorschoten (NL)

(73) Assignee: Prosensa Technologies B.V., Leiden (NL)

( * ) Notice: Subject to any disclaimer, the term of this patent is extended or adjusted under 35 U.S.C. 154(b) by 0 days.

(21) Appl. No.: 12/684,534

(22) Filed: Jan. 8, 2010

(65) Prior Publication Data

US 2010/0184947 A1    Jul. 22, 2010

Related U.S. Application Data

(63) Continuation of application No. PCT/NL2008/050470, filed on Jul. 11, 2008.

(30) Foreign Application Priority Data

Jul. 12, 2007  (EP) .................................... 07112313

(51) Int. Cl.
  *A61K 38/10*    (2006.01)
  *C07K 5/12*     (2006.01)

(52) U.S. Cl.
  USPC ......................... 424/1.69; 514/21.5; 530/327

(58) Field of Classification Search
  None
  See application file for complete search history.

(56) References Cited

U.S. PATENT DOCUMENTS

| | | | |
|---|---|---|---|
| 5,034,506 A | 7/1991 | Summerton et al. | |
| 5,418,139 A | 5/1995 | Campbell | |
| 5,541,308 A | 7/1996 | Hogan et al. | |
| 5,593,974 A | 1/1997 | Rosenberg et al. | |
| 5,608,046 A | 3/1997 | Cook et al. | |
| 5,627,263 A | 5/1997 | Ruoslahti et al. | |
| 5,658,764 A | 8/1997 | Pergolizzi et al. | |
| 5,741,645 A | 4/1998 | Orr et al. | |
| 5,766,847 A | 6/1998 | Jackle et al. | |
| 5,853,995 A | 12/1998 | Lee | |
| 5,869,252 A | 2/1999 | Bouma et al. | |
| 5,916,808 A | 6/1999 | Kole et al. ....................... 435/375 |
| 5,962,332 A | 10/1999 | Singer et al. | |
| 5,968,909 A | 10/1999 | Agrawal et al. | |
| 5,976,879 A | 11/1999 | Kole et al. ....................... 435/375 |
| 6,124,100 A | 9/2000 | Jin | |
| 6,130,207 A | 10/2000 | Dean et al. | |
| 6,133,031 A * | 10/2000 | Monia et al. ................... 435/375 |
| 6,172,208 B1 | 1/2001 | Cook ........................... 536/23.1 |
| 6,172,216 B1 | 1/2001 | Bennett et al. | |
| 6,210,892 B1 | 4/2001 | Bennett et al. ..................... 435/6 |
| 6,251,589 B1 | 6/2001 | Tsuji et al. | |
| 6,280,938 B1 | 8/2001 | Ranum et al. | |
| 6,300,060 B1 | 10/2001 | Kantoff et al. | |
| 6,322,978 B1 | 11/2001 | Kahn et al. | |
| 6,329,501 B1 | 12/2001 | Smith et al. | |
| 6,355,481 B1 | 3/2002 | Li et al. | |
| 6,355,690 B1 | 3/2002 | Tsuji | |
| 6,369,038 B1 | 4/2002 | Blumenfeld et al. | |
| 6,379,698 B1 | 4/2002 | Leamon | |
| 6,399,575 B1 | 6/2002 | Smith et al. | |
| 6,514,755 B1 | 2/2003 | Ranum et al. | |
| 6,623,927 B1 | 9/2003 | Brahmachari et al. | |
| 6,653,466 B2 | 11/2003 | Matsuo | |
| 6,653,467 B1 | 11/2003 | Matsuo et al. | |
| 6,670,461 B1 | 12/2003 | Wengel et al. | |
| 6,727,355 B2 | 4/2004 | Matsuo et al. ................. 536/24.5 |
| 6,743,893 B2 * | 6/2004 | Engler et al. .................. 530/300 |
| 6,794,192 B2 | 9/2004 | Parums et al. | |
| 6,902,896 B2 | 6/2005 | Ranum et al. | |
| 6,982,150 B2 | 1/2006 | Sheetz et al. | |
| 7,001,994 B2 | 2/2006 | Zhu ................................. 536/4.1 |
| 7,118,893 B2 | 10/2006 | Ranum et al. | |
| 7,189,530 B2 | 3/2007 | Botstein et al. | |
| 7,202,210 B2 | 4/2007 | Wolfman et al. | |
| 7,250,404 B2 | 7/2007 | Felgner et al. | |
| 7,355,018 B2 | 4/2008 | Glass | |
| 7,405,193 B2 | 7/2008 | Lodish et al. ....................... 514/2 |

(Continued)

FOREIGN PATENT DOCUMENTS

| | | |
|---|---|---|
| CA | 2319149 | 10/2001 |
| CA | 2526893 A1 | 11/2004 |
| EP | 438512 A1 | 7/1991 |
| EP | 558697 | 9/1993 |
| EP | 614977 A2 | 9/1994 |
| EP | 850300 | 7/1998 |
| EP | 1054058 | 5/2000 |
| EP | 1015628 A1 | 7/2000 |
| EP | 1133993 | 9/2001 |
| EP | 1160318 | 12/2001 |

(Continued)

OTHER PUBLICATIONS

Wang et al. Adeno-associated virus vector carrying human minidystrophin genes effectively ameliorates muscular dystrophy in mdx mouse model, Dec. 5, 2000, P.N.A.S. 97(25):13714-13719.*

(Continued)

*Primary Examiner* — John Ulm
(74) *Attorney, Agent, or Firm* — Sunstein Kann Murphy & Timbers LLP

(57) ABSTRACT

The invention provides conjugates, comprising an organ, tissue or tumor cell homing molecule linked to a moiety. Such a moiety can be, for example, an oligonucleotide, small interfering RNA, gene, virus, protein, pharmaceutical or detectable agent. In addition the invention provides methods to diagnose or treat neuronal or neuromuscular disease, or a pathology of the brain, or a tumor of neuronal or neuroectodermal origin, by administrating to a subject having or suspected of having a pathology a molecule or conjugate that homes to, binds to and is taken up by the brain cells or neuronal cells, or by the tumor cells of neuronal or neuroectodermal origin. The invention also provides a method of identifying and measuring neurite growth in neuronal cells.

7 Claims, 1 Drawing Sheet

(56) References Cited

U.S. PATENT DOCUMENTS

| | | | |
|---|---|---|---|
| 7,442,782 B2 | 10/2008 | Ranum et al. | 536/23.1 |
| 7,514,551 B2 | 4/2009 | Rabbani et al. | 536/26.6 |
| 7,534,879 B2 | 5/2009 | van Deutekom | 536/24.5 |
| 7,589,189 B2 | 9/2009 | Ichiro et al. | 536/24.5 |
| 7,655,785 B1 | 2/2010 | Bentwich | 536/24.1 |
| 7,771,727 B2 | 8/2010 | Fuselier et al. | 424/185.1 |
| 7,807,816 B2 | 10/2010 | Wilton et al. | 536/24.5 |
| 7,902,160 B2 | 3/2011 | Matsuo et al. | 514/44 |
| 7,960,541 B2 | 6/2011 | Wilton et al. | 536/24.5 |
| 8,232,384 B2 | 7/2012 | Wilton et al. | 536/24.5 |
| 2001/0056077 A1 | 12/2001 | Matsuo | |
| 2002/0049173 A1 | 4/2002 | Bennett et al. | |
| 2002/0055481 A1 | 5/2002 | Matsuo et al. | |
| 2002/0115824 A1 | 8/2002 | Engler et al. | |
| 2002/0165150 A1 | 11/2002 | Ben-Sasson | |
| 2003/0073215 A1 | 4/2003 | Baker et al. | |
| 2003/0082763 A1 | 5/2003 | Baker et al. | |
| 2003/0082766 A1 | 5/2003 | Baker et al. | |
| 2003/0109476 A1 | 6/2003 | Kmiec et al. | |
| 2003/0124523 A1 | 7/2003 | Asselbergs et al. | |
| 2003/0134790 A1 | 7/2003 | Langenfeld | |
| 2003/0235845 A1 | 12/2003 | van Ommen et al. | |
| 2003/0236214 A1 | 12/2003 | Wolff et al. | |
| 2004/0101852 A1 | 5/2004 | Bennett et al. | |
| 2004/0132684 A1 | 7/2004 | Sampath et al. | |
| 2004/0226056 A1 | 11/2004 | Roch et al. | |
| 2005/0096284 A1 | 5/2005 | McSwiggen | |
| 2005/0222009 A1* | 10/2005 | Lamensdorf et al. | 514/7 |
| 2005/0246794 A1 | 11/2005 | Khvorova et al. | |
| 2005/0277133 A1 | 12/2005 | McSwiggen | |
| 2006/0074034 A1 | 4/2006 | Collins et al. | |
| 2006/0148740 A1 | 7/2006 | Platenburg | 514/44 |
| 2007/0082861 A1 | 4/2007 | Matsuo et al. | |
| 2007/0141628 A1 | 6/2007 | Cunningham et al. | 435/7.1 |
| 2007/0275914 A1 | 11/2007 | Manoharan et al. | |
| 2007/0292408 A1 | 12/2007 | Singh et al. | |
| 2008/0015158 A1 | 1/2008 | Ichiro et al. | |
| 2008/0039418 A1 | 2/2008 | Freier | |
| 2008/0113351 A1 | 5/2008 | Naito et al. | |
| 2008/0207538 A1 | 8/2008 | Lawrence et al. | 514/41 |
| 2008/0249294 A1 | 10/2008 | Haeberli et al. | 536/24.5 |
| 2010/0081627 A1 | 4/2010 | Sampath et al. | 514/47 |
| 2010/0099750 A1 | 4/2010 | McSwiggen et al. | 514/44 R |
| 2011/0015258 A1 | 1/2011 | Wilton et al. | 514/44 R |
| 2012/0029057 A1 | 2/2012 | Wilton et al. | 514/44 A |
| 2012/0029058 A1 | 2/2012 | Wilton et al. | 514/44 A |
| 2012/0041050 A1 | 2/2012 | Wilton et al. | 514/44 A |

FOREIGN PATENT DOCUMENTS

| | | | |
|---|---|---|---|
| EP | 1191097 | 3/2002 | |
| EP | 1191098 | 3/2002 | |
| EP | 1380644 | 1/2004 | |
| EP | 1 487 493 A2 | 12/2004 | |
| EP | 1495769 | 1/2005 | |
| EP | 1501931 | 2/2005 | |
| EP | 1544297 | 6/2005 | |
| EP | 1567667 A1 | 8/2005 | |
| EP | 1568769 | 8/2005 | |
| EP | 1619249 | 1/2006 | |
| EP | 1857548 A1 | 11/2007 | |
| KR | 20030035047 | 5/2003 | |
| WO | WO-9301286 A2 | 1/1993 | |
| WO | WO-9516718 A1 | 6/1995 | |
| WO | WO-9530774 A1 | 11/1995 | |
| WO | WO-9712899 | 4/1997 | |
| WO | WO-9730067 | 8/1997 | |
| WO | WO-9818920 A1 | 5/1998 | |
| WO | WO-9849345 A1 | 11/1998 | |
| WO | WO 98/53804 | 12/1998 | A61K 31/00 |
| WO | WO-0179283 A1 | 10/2001 | |
| WO | WO 01/83503 | 11/2001 | C07H 21/00 |
| WO | WO-0183695 A2 | 11/2001 | |
| WO | WO-0202406 | 1/2002 | |
| WO | WO-0224906 | 3/2002 | |
| WO | WO-0226812 A1 | 4/2002 | |
| WO | WO-0229056 | 4/2002 | |
| WO | WO-03002739 | 1/2003 | |
| WO | WO-03/014145 A2 | 2/2003 | |
| WO | WO-03013437 A2 | 2/2003 | |
| WO | WO-03037172 | 5/2003 | |
| WO | WO-03095647 | 11/2003 | |
| WO | WO-2004/011060 A2 | 2/2004 | |
| WO | WO-2004015106 | 2/2004 | |
| WO | WO-2004016787 | 2/2004 | |
| WO | WO 2004/037854 | 5/2004 | C07K 1/04 |
| WO | WO-2004048570 | 6/2004 | |
| WO | WO-2004083432 | 9/2004 | |
| WO | WO-2004083446 | 9/2004 | |
| WO | WO-2004101787 A1 | 11/2004 | |
| WO | WO-2004108157 | 12/2004 | |
| WO | WO-2004108157 A2 | 12/2004 | |
| WO | WO 2005/023836 | 3/2005 | |
| WO | WO-2005019453 A2 | 3/2005 | |
| WO | WO2005/003550 A2 | 4/2005 | |
| WO | WO-2005085476 A1 | 9/2005 | |
| WO | WO-2005086768 | 9/2005 | |
| WO | WO-2005105995 A2 | 11/2005 | |
| WO | WO-2005115439 | 12/2005 | |
| WO | WO-2005116204 A1 | 12/2005 | |
| WO | WO-2006000057 | 1/2006 | |
| WO | WO-2006007910 | 1/2006 | |
| WO | WO-2006017522 | 2/2006 | |
| WO | WO-2006031267 A2 | 3/2006 | |
| WO | WO-2006/054262 A2 | 5/2006 | |
| WO | WO-2006083800 A2 | 8/2006 | |
| WO | WO2006/108052 A2 | 10/2006 | |
| WO | WO-2006112705 | 10/2006 | |
| WO | WO-2006121960 A2 | 11/2006 | |
| WO | WO-2007002904 A2 | 1/2007 | |
| WO | WO-2007044362 A2 | 4/2007 | |
| WO | WO-2007089584 A2 | 8/2007 | |
| WO | WO-2007089611 A2 | 8/2007 | |
| WO | WO-2007123402 A2 | 11/2007 | |
| WO | WO-2007135105 A1 | 11/2007 | |
| WO | WO-2008011170 A2 | 1/2008 | |
| WO | WO-2008018795 A1 | 2/2008 | |
| WO | WO-2008021136 A2 | 2/2008 | |

OTHER PUBLICATIONS

Lee et al., "Receptor mediated uptake of peptides that bind the human transferrin receptor", Eur. J. Biochem. 268, 2004-2012 (2001).

International Search Report for corresponding PCT application. (WO2009/008725 A3), mailed Feb. 7, 2009.

Aartsma-Rus et al. "Antisense Mediated exon skipping; A Versatile Tool with Therapeutic and Research Applications" RNA 2007 pp. 1609-1624 vol. 13 No. 10.

Aartsma-Rus et al. Antisense-Induced Exon Skipping for Duplications in Duchenne Muscular Dystrophy Jul. 5, 2007 BMC Med. Genet. 8:43.

Aartsma-Rus et al. Therapeutic Modulation of DMD splicing by Blocking Exonic Splicing Enhancer Sites with Antisense Oligonucleotides Ann NY Acad Sci 2006 pp. 74-76 vol. 1082.

Aartsma-Rus, et al., "Functional Analysis of 114 Exon-Internal AONs for Targeted DMD Exon Indication for Steric Hindrance of SR Protein Binding Sites," Oligonucleotides, 2005, pp. 284-297, vol. 15.

Aartsma-Rus, et al., Antisense-Induced Multiexon Skipping for Duchenne Muscular Dystrophy Makes More Sense, Am. J. Hum. Genet, 2004 pp. 83-92, vol. 74.

Aartsma-Rus, et al., Exploring the Frontiers of Therapeutic Exon Skipping for Duchenne Muscular Dystrophy by Double Targeting within One or Multiple Exons, Molecular Therapy, 2006, pp. 1-7.

Aartsma-Rus, et al., Targeted exon skipping as a potential gene correction therapy for Duchenne muscular dystrophy, Neuromuscular Disorders, 2002, S71-S77, vol. 12.

Aartsma-Rus, et al., Therapeutic antisense-induced exon skipping in cultured muscle cells from six different patients, Human Molecular Genetics, 2003, pp. 907-914, vol. 12, No. 8.

(56) References Cited

OTHER PUBLICATIONS

Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.

Agrawal and Kandimalla, et al., "Antisense therapeutics: is it as simple as complementary base recognition?" Mol. Med. Today, Feb. 2000, vol. 6., pp. 72-81.

Anderson et al., Correlated NOS-I[mu] and myf5 expression by satellite cells in mdx mouse muscle regeneration during NOS manipulation and deflazacort treatment. Neuromusccular Disorders, Jun. 2003, vol. 13(5): 388-396.

Arruda V R, The role of immunosuppression in gene and cell based treatments for Duchenne Muscular Dystrophy. Molecular Therapy, Jun. 2007, vol. 15(6): 1040-1041.

Arzumanov, et al. Inhibition of HIV-1 Tat-dependent trans activation by steric block chimeric 2'-O-methyl/LNA oligoribonucleotides. Biochemistry, 2001, vol. 40, pp. 14645-14654.

Austin et al. "Cloning and characterization of alternatively spliced isoforms of Dp71." Hum Mol Genetics 1995 vol. 4 No. 9 1475-1483.

Australian Office Action for AU 2009240879, dated Jun. 22, 2011.

Barabino et al. (1992) "Antisense probes targeted to an internal domain in US snRNP specifically inhibit the second step of pre-mRNA splicing" Nucleic Acids Res. 20(17):4457-4464.

Bionity.Com News-Center, Leiden University Medical Center and Prosensa B.V. Announce First Successful Clinical Study with RNA-based Therapeutic PRO051, dated Jan. 3, 2008, <http://www.bionity.com/news/e/76185>.

Biopharmaceutiques, Merging Pharma & Biotech, Edition 48, Jan. 10, 2008. <http://www.biopharmaceutiques.com/en/num>, visited Jan. 11, 2008.

Bremmer-Bout, et al., Targeted exon skipping in transgenic hDMD mice: A model for direct preclinical screening of human-specific antisense oligonucleotides. Mol Ther. Aug. 2004; 10(2):232-40.

Brown, et al., "Structure and mutation of the dystrophin gene" in Dystrophin: Gene, protein and cell biology, (Brown and Lucy, eds). Cambridge University Press, Cambridge, 1997, pp. 1-16.

Canadian Office Action for CA 2,524,255, dated Jul. 6, 2011.

Cartegni, et al., Abstract, Listening to silence and understanding nonsense: exonic mutations that affect splicing, Nature Reviews Genetics, Apr. 2002, pp. 285-298, vol. 3.

Chaubourt et al., Muscular nitric oxide synthase ([mu]NOS) and utrophin. J. of Physiology Paris, Jan.-Mar. 2002; vol. 96(1-2): 43-52.

Coulter et al. Identification of a new class of exonic splicing enhancers by in vivo selection. Mol. Cell. Biol. 17(4) 2143-50 (1997).

Crooke. in Basic Principles of Antisense Therapeutics, Springer-Verlag, Eds, New York, 1998, pp. 1-50.

Dahlqvist, et al., "Functional notch signaling is required for BMP4-induced inhibition of myogenic differentiation," Development 130:6089-6099 (2003).

De Angelis, et al., Chimeric snRNA molecules carrying antisense sequences against the splice junctions of exon 51 of the dystrophin pre-mRNA exon skipping and restoration of a dystrophin synthesis in delta 48-50 DMD cells, PNAS, Jul. 9, 2002, pp. 9456-9461, vol. 99, No. 14.

Declaration of Dr. Adrian Krainer (submitted in Third Party's Stmt for JP Appl. No. 2002-529499, dated Oct. 29, 2010).

Dickson, et al., Screening for antisense modulation of dystrophin pre-mRNA splicing, Neuromuscul. Disord., 2002, S67-70, Suppl. 1.

Dirkson, et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.

Dunckley, et al., Modification of splicing in the Dsytrophin gene in cultured Mdx muscle cells by antisense oligoribonucleotides. Hum Mol Genet. 1995 7(7):1083-90.

Dunckley, et al., Modulation of Splicing in the DMD Gene by Antisense Oligoribonucleotides, Nucleosides & Nucleotides, 1997, pp. 1665-1668, vol. 16, No. 7-9.

Erba et al., Structure, chromosome location, and expression of the human gamma-actin gene: differential evolution, location, and expression of the cytoskeletal beta- and gamma-actin genes. Mol. Cell. Biology, 1988, 8(4):1775-89.

Errington, et al., Target selection for antisense oligonucleotide induced exon skipping in the dystrophin gene. J Gene Med. Jun. 2003; 5(6):518-27.

Feener et al., Alternative splicing of human dystrophin mRNA generates isoforms at the carboxy terminus. Nature, 338 (6215): 509-511 (1989).

Flutter, K., "In Vivo tumor growth inhibition and biodistribution studies of locked nucleic acid (LNA) antisense oligonucleotides," Nucl. Acids Research 2003, vol. 31., No. 3., pp. 953-962.

Genes VII, Jan. 2000, Benjamin Lewin, Chapter 22, Nuclear Splicing, pp. 704-705.

Ginjaar, et al., Dystrophin nonsense mutation induces different levels of exon 29 skipping and leads to variable phenotypes within one BMD family, European Journal of Human Genetics (2000) 8, 793-796.

Grady, Promising Dystrophy Drug Clears Early Test, The New York Times, Dec. 27, 2007.

Granchelli et al., Pre-clinical screening of drugs using the mdx mouse. Neuromuscular Disorders, Pergamon Pres. vol. 10(4-5): 235-239, Jun. 2000.

Gryaznov, "Oligonucleotide N3'→ P5' phosphoramidates as potential therapeutic agents." Biochemistry et Biophys. Acta, 1999, vol. 1489, pp. 131-140/.

Hagiwara, et al. "A novel point mutation (G-1 to T) in a 5' splice donor site of intron 13 of the dystrophin gene results in exon skipping and is responsible for Becker muscular dystrophy." Am J. Hum Genet. Jan. 1994;54(1):53-61.

Hoffman, Skipping toward Personalized Molecular Medicine, N. England J. Med., Dec. 27, 2007, pp. 2719-2722, vol. 357, No. 26.

Hussey, et al., Analysis of five Duchenne muscular dystrophy exons and gender determination using conventional duplex polymerase chain reaction on single cells, Molecular Human Reproduction, 1999, pp. 1089-1094, vol. 5, No. 11.

Iezzi, et al. "Deacetylase inhibitors increase muscle cell size by promoting myoblast recruitment and fusion through induction of follistation," Development Cell 6:673-684 (2004).

International Preliminary Examination Report, International Application No. PCT/NL01/00697, dated Aug. 1, 2002.

International Search Report, International Application No. PCT/NL2008/050470, dated Jul. 2, 2009.

International Search Report, International Application No. PCT/NL2008/050475, dated Jun. 25, 2009.

International Search Report, International Application No. PCT/NL2008/050673, dated Feb. 9, 2009.

International Search Report, International Application No. PCT/NL01/00697, dated Dec. 21, 2002.

International Search Report, International Application No. PCT/NL2004/000196, dated Oct. 28, 2004.

International Search Report, International Application No. PCT/NL2006/000209, dated Oct. 5, 2006.

Karras, et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.

Kerr, et al., "Bmp Regulates Skeletal Myogenesis at Two Steps," Molecular Cellular Proteomics 2.9:976. 123.8 (2003) (Abstract Only).

Kurrek, et al., "Design of antisense oligonucleotides stabilized by locked nucleic acids." Nucleic Acids Research, 2002, vol. 30, No. 9, pp. 1911-1918.

Laptev et al., (1994) "Specific inhibition of expression of a human collagen gene (COL1A1) with modified antisense oligonucleotides. The most effective target sites are clustered in double-stranded regions of the predicted secondary structure for the mRNA" Biochemistry 33(36):11033-11039.

Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.

(56) References Cited

OTHER PUBLICATIONS

Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).

Letter from Prosensa Therapeutics B.V. to Federal Agency for Medicines and Health Products dated Jan. 9, 2008, regarding A Phase I/II, open label, escalating dose, pilot study to assess the effect, safety, tolerability and pharmacokinetics of multiple subcutaneous doses of PRO051 in patients with Duchenne muscular dystrophy.

Liu et al., "A mechanism for exon skipping caused by nonsense or missense mutations in BRCA1 and other genes." Nat Genet. Jan. 2001;27(1):55-8.

Liu, et al., Identification of functional exonic splicing enhancer motifs recognized by individual SR proteins, Genes & Development, 1998, pp. 1998-2012, vol. 12.

Lu et al. Functional Amounts of Dystrophin Produced by Skipping the Mutated Exon in the MDX Dystrophic Mouse 2003 Nat Med 8: 1009-1014.

Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.

LUMC and Prosensa report positive results of DMD study, Pharmaceutical Business Review Online, dated Dec. 28, 2007, <http://www.pharmaceutical-business-review.com/article_news_print.asp?guid=8462FD44-F35D-4EOB-BC>.

Mann, et al., Antisense-induced exon skipping and synthesis of dystrophin in the mdx mouse. Proc Natl Acad Sci USA Jan. 2, 2001: 98(1):42-7.

Mann, et al., Improved antisense oligonucleotide induced exon skipping in the mdx mouse model of muscular dystrophy. J Gene Med. Nov.-Dec. 2002:4(6):644-54.

Matsuo et al. (1992) "Partial deletion of a dystrophin gene leads to exon skipping and to loss of an intra-exon hairpin structure from the predicted mRNA precursor" Biochem. Biophys. Res. Commun. 182(2):495-500.

Matsuo, et al., "Duchenne/Becker muscular dystrophy: from molecular diagnosis to gene therapy." Brain Dev. (1996) 18(3):167-172.

McClorey et al. Induced Dystrophin Exon Skipping in Human Muscle Explants Neuromuscul Disord 2006 pp. 583-590 vol. 16 No. 9-10.

Monaco, et al., An Explanation for the Phenotypic Differences between Patients Bearing Partial Deletions of the DMD Locus, Genomics, 1988, pp. 90-95, vol. 2.

Moon, et. al., "Target site Search and effective inhibition of leukaemic cell growth by a covalently closed multiple anti-sense oligonucleotide to c-myb" The Biochemical Journal, Mar. 1, 2000, vol. 346 Pt 2, pp. 295-303.

Munroe (1988) "Antisense RNA inhibits splicing of pre-mRNA in vitro" EMBO J. 7(8):2523-2532.

Muntoni et al. "A Mutation in the Dystrophin Gene Selectively Affecting Dystrophin Expression in the Heart." *J. Clin Invest.* vol. 96 Aug. 1995. 693-699.

Neuner Behandlungsansatz bei seltener Muskelkrankheit, NZZ Online, visited Feb. 20, 2008, <http://www.nzz.ch/nachrichten/wissenschaft/neuner_behandlungsansatz_bei_seltener_muskelkrankheit_1.64>.

New Clinical Trial Results Show How Personalized Medicine Will Alter Treatment of Genetic Disorders, Medical News Today, Dec. 29, 2007 <http://www.medicalnewstoday.com/article/92777.php>.

Nishio, et al., Identification of a novel first exon in the human dystrophin gene and of a new promoter located more than 500 kb upstream of the nearest known promoter. (1994) J. Clin. Invest. 94:1037-1042.

Notice of Opposition filed against EP 1 619 249 B, dated Jun. 23, 2009.

Office Action for U.S. Appl. No. 10/395,031, dated Apr. 2, 2009.

Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.
Office Action for U.S. Appl. No. 10/395,031, dated May 30, 2008.
Office Action for U.S. Appl. No. 10/395,031, dated Nov. 30, 2006.
Office Action for U.S. Appl. No. 10/395,031, dated Oct. 16, 2009.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated May 29, 2009.
Office Action for U.S. Appl. No. 11/233,507, dated Nov. 12, 2008.
Office Action for U.S. Appl. No. 11/982,285, dated May 4, 2009.
Office Action for U.S. Appl. No. 11/982,285, dated Sep. 18, 2009.

Opalinska and Gewirtz. "Nucleic-acid therapeutics: basic principles and recent applications." Nature Reviews Drug Discovery, 2002, vol. 1, pp. 503-514.

Patel, et al., "The Function of Myostatin and strategies of Myostatin blockade-new hope for therapies aimed at promoting growth of skeletal muscle," Neuromuscular Disorders 15(2):117-126 (2005).

Pramono, et al., Abstract, Induction of Exon Skipping of the Dystrophin Transcript in Lymphoblastoid Cells by Transfecting an Antisense Oligodeoxynucleotide Complementary to an Exon Recognition Sequence, Biochemical and Biophysical Research Communications, Sep. 13, 1996, pp. 445-449, vol. 226, No. 2.

Radley et al., Duchenne muscular dystrophy: Focus on pharmaceutical and nutritional interventions. International J. of Biochem. and Cell Biol., vol. 39(3):469-477, Oct. 2006.

Rando, Thomas A., "Oligonucleotide-mediated gene therapy for muscular dystrophies." Neuromuscular Disorders, 2002, vol. 12, pp. S55-S60.

Request for an Opinion under Section 74(A) in relation to Patent No. EP (UK) 1 619 249B in the name of Academisch Ziekenhuis Leiden, opinion issued on Jun. 4, 2009.

Request for UK IPO Opinion (Section 74A & Rule 93)—EP(UK) 1619249 dated Mar. 9, 2009.

Roberts et al., Direct detection of dystrophin gene rearrangements by analysis of dystrophin mRNA in peripheral blood lymphocytes. Am. J. Hum. Genet. 49(2): 298-310 (1991).

Roberts, et al., "Exon structure of the human dystrophin gene." Genomics, 1993, vol. 16, No. 2, pp. 536-538. (1993).

Roberts, et al., Direct diagnosis of carriers of Duchenne and Becker muscular dystrophy by amplification of lymphocyte RNA. Lancet, 336 (8730-8731): 1523-6 (1990).

Roberts, et al., Searching for the 1 in 2,400,000: a review of dystrophin gene point mutations. Hum. Mut. 4:1-11 (1994).

Rolland et al., Overactivity of exercise-sensitive cation channels and their impaired modulation by IGF-1 in mdx native muscle fibers: beneficial effect of pentoxifylline. Dec. 2006; Epub Sep. 28, Neurobiology Disease, vol. 24(3): 466-474.

Scanlon, "Anti-genes: siRNA, ribozymes, and antisense." Curr. Pharmaceutical Biotechnology, 2004, vol. 5, pp. 415-420.

Segalat et al., Capon expression in skeletal muscle is regulated by position, repair, NOS activity, and dystrophy. Experimental Cell Research, Jan. 2005, vol. 302(2): 170-179.

Sertic, et al., "Deletion screening of the Duchenne/Becker muscular dystrophy gene in Croatian population" Coll. Antropol. 1997, 1:151-156.

Shapiro and Senapathy, "RNA splice junctions of different classes of eukaryotes: sequence statistics and functional implications in gene expression." Nucleic Acids Research, 1987, vol. 15. No. 17, pp. 7155-7174.

Sherratt, et al., Exon Skipping and Translation in Patients with Frameshift Deletions in the Dystrophin Gene, Am. J. Hum. Genet, 1993, pp. 1007-1015, vol. 53.

Shiga, et al., Disruption of the Splicing Enhancer Sequence within Exon 27 of the Dystrophin Gene by a Nonsense Mutation Induces Partial Skipping of the Exon and Is Responsible for Becker Muscular Dystrophy, J. Clin. Invest., Nov. 1997, pp. 2204-2210, vol. 100, No. 9.

Simoes-Wust, et al., bcl-xL Antisense Treatment Induces Apoptosis in Breast Carcinoma Cells, Int. J. Cancer, 2000, pp. 582-590, vol. 87.

(56) References Cited

OTHER PUBLICATIONS

Sterrenburg, et al., "Gene expression of profiling highlights defective myogenesis in DMD patients and a possible role for bone morphogenetic protein 4," Neurobiology of Disease 23(1):228-236 (2006).
Surono et al. Chimeric RNA/ethylene-Bridged Nucleic Acids Promote Dystrophin Expression in Myocytes of Duchenne Muscular Dystrophy by Inducing Skipping of the Nonsense Mutation-Encoding Exon Hum Gene Ther. vol. 15(8) pp. 749-757 (2004).
Surono et al. "Six Novel Transcripts that Remove a Huge Intron Ranging from 250 to 800 kb Are Produced by Alternative Splicing of the 5' Region of the Dystrophin Gene in Human Skeletal Muscle." *BBRC* 239 895-899 (1997).
Suter, et al., Double-target antisense U7 snRNAs promote efficient skipping of an aberrant exon in three human B-thalassemic mutations, Human Molecular Genetics, 1999, pp. 2415-2423, vol. 8, No. 13.
Suwanmanee et al. (2002) "Restoration of Human b-globin Gene Expression in Murine and Human IVS2-654 Thalassemic Erythroid Cells by Free Uptake of Antisense Oligonucleotides" Mol. Pharmacology 62(3):545-553.
Takashima et al. Oligonucleotides Against a Splicing Enhancer Sequence Led to Dystrophin Production in Muscle Cells From a Duchenne Muscular Dystrophy Patient Brain Dev Dec. 2001; 23:788-90.
Takeshima, et al., Modulation of In Vitro Splicing of the Upstream Intron by Modifying an Intra-Exon Sequence Which is Deleted from the Dystrophin Gene in Dystrophin Kobe, J. Clin. Invest., Feb. 1995, pp. 515-520, vol. 95.
Tanaka, et al., Polypurine Sequences within a Downstream Exon Function as a Splicing Enhanced, Molecular and Cellular Biology, Feb. 1994, pp. 1347-1354, vol. 14, No. 2.
Thanh, et al., "Characterization of revertant muscle fibers in Duchenne muscular dystrophy, using exon-specific monoclonal antibodies against dystrophin." Am. J. Hum. Genet. 1995, vol. 56, pp. 725-731.
Third Party's Statement for Japan Appl. No. 2002-529499, dated Oct. 29, 2010.
Tian H, Kole R, "Selection of novel exon recognition elements from a pool of random sequences." Mol Cell Biol 15(11):6291-8. (1995).
Tsuchida "Peptides, Proteins & Antisense: the role of myostatin and bone morphogenetic proteins in muscular disorders," Expert Opinion of Biologica Therapy 6(2):147-153 (2006).
Van Deutekom et al. Advances in Duchenne Muscular Dystrophy Gene Therapy 2003 Nat Rev Genet 4(10): 774-83.
Van Deutekom, et al., Antisense-induced exon skipping restores dystrophin expression in DMD patient derived muscle cells. Hum Mol Genet. Jul. 15, 2001:10(15:1547-54).
Van Deutekom, et al., Local Dystrophin Restoration with Antisense Oligonucleotide PRO051, N. England J. Med., Dec. 27, 2007, pp. 2677-2686.
Verreault, et al. "GENE silencing in the development of personalized cancer treatment: the targets, the agents and the delivery systems." Curr. Gene Therapy, 2006, vol. 6, pp. 505-553.
Watakabe, at al., The role of exon sequences in splice site selection, Genes & Development, 1993, pp. 407-418, vol. 7.
Wells et al. Enhanced in Vivo Delivery of Antisense Oligonucleotide to Restore Dystrophin Expression in Adult MDX Mouse Muscle FEBS Letters 2003 552: 145-149.
Wheway and Roberts. "The Dystrophin Lymphocyte promoter revisited: 4.5-megabase intron, or artefact?" *Neuromuscular Disorders* 13(2003) 17-20.
Wilton, et al., "Specific removal of the nonsense mutation from the mdx dystrophin protein mRNA using antisense oligonucleotides." Neuromuscular Disorders, 1999, vol. 9, pp. 330-338.
Wilton, et al., "Antisense oligonucleotides, exon skipping and the dystrophin gene transcript," Acta Myologica XXIV:222-229 (2005).
Zhou et al., Current understanding of dystrophin-related muscular dystrophy and therapeutic challenges ahead. Chinese Medical J., Aug. 2006, vol. 119(16): 1381-1391.

Aartsma-Rus et al. "Guidelines for Antisense Oligonucleotide Design and Insight into Splice-modulation Mechanisms." *Molecular Therapy 2009* pp. 548-553 (Published Online Sep. 23, 2008).
Alter et al., "Systemic delivery of morpholino oligonucleotide restores dystrophin expression bodywide and improves dystrophic pathology." Nature Medicine. Feb. 2006;12(2):175-7. Epub Jan. 29, 2006.
Arechavala-Gomeza et al. "Comparative Analysis of Antisense Oligonucleotide Sequences for Targeted Skipping of Exon 51 During Dystrophin pre-mRNA Splicing in Human Muscle" *Hum Gene Ther* 2007 pp. 798-810 vol. 18 No. 9.
Austin, et al., "Expression and synthesis of alternatively spliced variants of Dp71 in adult human brain." *Neuromuscular Disorders*. 10(2000) 187-193.
Barany "The ligase chain reaction in a PCR world." PCR Methods Appl. Aug. 1991;1(1):5-16.
Brett et al., 2000 EST comparison indicates 38% of human m RNAs contain possible alternative splice forms. FEBS Lett 474(1): 83-86.
Buck et al., "Design Strategies and Performance of Custom DNA Sequencing Primers" Biotechniques. 27:528-536, 1999.
Burnett, et al., "DNA sequence-specific polyamides alleviate transcription inhibition associated with long GAA. TTC repeats in Friedreich's ataxia," *PNAS*, 2006, pp. 11497-11502, vol. 103, No. 31.
Caplen, et al., "Rescue of polyglutamine-mediated cytotoxicity by double-stranded RNA-mediated RNA interference," *Human molecular genetics*, 2002, pp. 175-184, vol. 11, No. 2.
Denny et al., "Oligo-riboprobes. Tools for in situ hybridisation". Histochemistry (1988) 89:481-493.
Duboc et al., "Effect of Perindopril on the Onset and Progression of Left Ventricular Dysfunction in Duchenne Muscular Dystrophy." *Journal of Amer. Coll. Cardiology*, 45(6):855-7, Mar. 15, 2005.
European Office Action in corresponding application EP 05 076 770 dated Jan. 29, 2007.
Fu, et al., "An Unstable Triplet Repeat in a Gene Related to Myotonic Muscular Dystrophy", *Science*, vol. 255, 1256-1258. 1992.
Furling. et al., "Viral vector producing antisense RNA restores myotonic dystrophy myoblast functions", *Gene Therapy* (2003) 10, 795-802.
Galderisi, et al., "Myotonic dystrophy: antisense oligonucleotide inhibition of DMPK gene expression in vitro." *Biochem Biophys Res Commun* 221:750-754 (1996).
GenBank accession No. AZ993191.1, 2MO278E12F mouse 10kb plasmid UUGC2M library Mus muscu genomic clone UUGC2MO278E12F, genomic survey sequence, entry created and last updated on Apr. 27, 2001.
GenBank accession No. EW162121.1, rfat0126_k17.y1 fat Sus scrofa cDNA5-, mRNA sequence, entry created on Aug. 13, 2007, last updated on Mar. 3, 2011.
Grady, Early drug test shows promise in treating muscular dystrophy, International Herald Tribune, Jan. 3, 2008, Health & Science, p. 9.
Handa, et al., "The AUUCU repeats responsible for spinocerebellar ataxia type 10 form unusual RNA hairpins." *Journal of Biological Chemistry* 280(32):29340-29345 (2005).
Hansen, Product Development—Addition by subtraction, BioCentury, The Bernstein Report on BioBusiness, Jan. 7, 2008, p. A28 of 38.
Hasholt, et al., "Antisense downregulation of mutant huntingtin in a cell model," *Journal of Gene Medicine*, 2003, pp. 528-538, vol. 5, No. 6.
Highfield "Science: Boffin log", The Daily Telegraph, http://www.telegraph.co.uk/science/science-news/3320286/Science-Boffin-log.html, (Hope for Muscular Dystrophy Drug) Jan. 1, 2008.
Hoffman, et al.,"Somatic reversion/suppression of the mouse *mdx* phenotype in vivo." *J. of the Neurological Sciences*, 1990, 99: 9-25.
Ikezawa et al. "Dystrophin gene analysis on 130 patients with Duchenne Muscular dystrophy with a special reference to muscle mRNA analysis." Brain & Develop. 20:165-168, 1998.
International Preliminary Report on Patentability and Written Opinion for PCT/EP2007/054842, mailed on Nov. 21, 2008, 8 pages.
International Search Report for PCT/EP2007/054842, mailed on Aug. 21, 2007, 3 pages.

(56) References Cited

OTHER PUBLICATIONS

Ito, et al., "Purine-Rich Exon Sequences Are Not Necessarily Splicing Enhancer Sequence in the Dystrophin Gene." *Kobe J. Med. Sci.* 47, 193/202, Oct. 2001.

Langlois, et al., "Hammerhead ribozyme-mediated destruction of nuclear foci in myotonic dystrophy myoblasts," *Molecular therapy*, 2003, pp. 670-680, vol. 7, No. 5.

Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutan.

Liu, et al., "Specific inhibition of Huntington's disease gene expression by siRNAs in cultured cells", *Proc. Japan Acad.* 79, Ser. B (2003), 293-298.

Matsuo, et al., Exon Skipping during Splicing of Dystrophin mRNA Precursor due to an Intraexon Deletion in the Dystrophin Gene of Duchenne Muscular Dystrophe Kobe. *J. Clin. Invest.* 87, 2127-2131. 1991.

Muntoni, et al., 149th ENMC International Workshop and 1st TREAT-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol.

O'Shaughnessy et al., "Superior Survival With Capecitabine Plus Docetaxel Combination Therapy in Anthracycline-Pretreated Patients With Advanced Breast Cancer: Phase III Trial Results." *Journal of Clinical Oncology*, vol. 20, No. 12 Jun. 15, 2002: pp. 2812.

Oxford Dictionary of English, 2nd Edition, Revised, Oxford University Press, p. 158. 2005.

Patentee's response to communication dated Jul. 29, 2009 from the Opposition Division of EPO in related European Patent Application (EP 05 076 770.6), dated Jan. 27, 2010.

Politano et al., "Gentamicin administration in Duchenne patients with Premature stop codon. Preliminary results." Acta Myologica 22:15-21, 2003.

Reitter B. "Deflazacort vs. prednisone in Duchenne muscular dystrophy: trends of an ongoing study." Brain Dev. 1995;17 Suppl:39-43.

Rosen et al., "Combination Chemotherapy and Radiation Therapy in the Treatment of Metastatic Osteogenic Sarcoma." *Cancer* 35: 622-630, 1975.

Smith et al., "Muscle-specific peptide #5", Mar. 23, 1999. From http://www.ebi.ac.uk/cgi-bin/epo/epofetch?AAW89659, downloaded Jul. 16, 2007. XP 002442550.

Takeshima et al "Intravenous Infusion of an Antisense Oligonucleotide Results in Exon Skipping in Muscle Dystrophin mRNA of Duchenne Muscular Dystrophy." Pediatric Research. May 2006, 59, 5, p. 690-694.

Van Oommnen (2008) The Therapeutic Potential of Antisense-Mediated Exon-Skipping Curr Opin Mol. Ther vol. 10(2) pp. 140-149.

Verhaart et al., "Prednisolone treatment does not interfere with 2'-O-methyl phosphorothioate antisense-mediated exon skipping in Duchenne muscular dystrophy." *Hum Gene Ther.* Mar. 2012;23(3):262-73. Epub Jan. 26, 2012.

Vickers, et al., "Efficient reduction of target RNAs by small interfering RNA and RNase H-dependent antisense agents. A comparative analysis." *J. Biol. Chem.* 278(9):7108-7118 (2003).

Wang et al. "Adeno-associated virus vector carrying human minidystrophin genes effectively ameliorates muscular dystrophy in mdx mouse model", Dec. 5, 2000, P.N.A.S. 97(25):13714-13719.

Yen, et al., "Sequence-specific cleavage of Huntingtin MRNA by catalytic DNA," *Animals of Neurology*, 1999, pp. 366-373, vol. 46, No. 3.

Reuser et al., "Uptake and Stability of Human and Bovine Acid α-Glucosidase in Cultured Fibroblasts and Skeletal Muscle Cells from Plycogenosis Type II Patients," Experimental Cell Research, vol. 155, pp. 178-189 (1984).

Wenk et al., "Quantitation of MR 46000 and MR 300000 mannose 6-phosphate receptors in human cells and tissues," Biochem Int., vol. 23, No. 4, pp. 723-731 (Mar. 1991) (Abstract).

Hyndman AG, "High affinity binding of transferrin in cultures of embryonic neurons from the chick retina," Brain Research, vol. 564, pp. 127-131 (1991).

Bijvoet et al., "Recombinant human acid α-glucosidase: high level production in mouse milk, biochemical characteristics, correction of enzyme deficiency in GSDII KO mice," Human Molecular Genetics, vol. 7(11), pp. 1815-1824 (1998).

Samoylova et al., "Elucidation of Muscle-Binding Peptides by Phage Display Screening," Muscle & Nerve, vol. 22, pp. 460-466, Apr. 1999.

Varani et al., "The GU wobble base pair, A fundamental building block of RNA structure crucial to RNA function in diverse biological systems," EMBO reports, vol. 1(1), pp. 18-23 (2000).

Martiniuk et al., "Correction of glycogen storage disease type II by enzyme replacement with a recombinant human acid maltase produced by over-expression in a CHO-DHFR(neg) cell line.," Biochem Biophys Res Commun., vol. 276(3), pp. 917-923, Oct. 5, 2000 (Abstract).

Zhang et al., "Efficient expression of naked dna delivered intraarterially to limb muscles of nonhuman primates.," Hum Gene Ther., vol. 12(4), pp. 427-438, Mar. 1, 2001 (Abstract).

Brown MD et al., "Gene delivery with synthetic (non viral) carriers.," Int J Pharm., 229(1-2), pp. 1-21, Oct. 23, 2001 (Abstract).

Arap et al., "Steps toward mapping the human vasculature by phage display," Nature Publishing Group, Nature Medicine, vol. 8(2), pp. 121-127, Feb. 2002.

European Patent Office, International Preliminary Examination Report, International Application No. PCT/NL01/00697 dated Aug. 1, 2002, 2 pages.

Hassan AB, "Keys to the Hidden Treasures of the Mannose 6-Phosphate/Insulin-Like Growth Factor 2 Receptor," American Journal of Pathology, vol. 162(1), pp. 3-6, Jan. 2003.

Lu et al., "Non-viral gene delivery in skeletal muscle: a protein factory," Gene Therapy, vol. 10, pp. 131-142 (2003).

Ghosh et al., "Mannose 6-Phosphate Receptors: New Twists in the Tale," Nature Reviews Molecular Cell Biology, vol. 4, pp. 202-212, Mar. 2003.

Gollins et al., "High-efficiency plasmid gene transfer into dystrophic Muscle," Gene Therapy, vol. 10, pp. 504-512 (2003).

Weisbart RH et al., "Cell type specific targeted intracellular delivery into muscle of a monoclonal antibody that binds myosin IIb.," Mol Immunol., vol. 39(13), pp. 783-789, Mar. 2003 (Abstract).

European Patent Office, Partial European Search Report for European Patent Application No. EP 030777205 dated Dec. 10, 2003, 5 pages.

European Patent Office, European Search Report Annex for European Patent Application No. EP 030777205 dated Dec. 10, 2003, 1 page.

Garcia-Blanco et al., "Alternative splicing in disease and therapy," Nature Biotechnology, vol. 22(5), pp. 535-546, May 2004.

Aartsma-Rus et al., "Comparative analysis of antisense oligonucleotide analogs for targeted DMD exon 46 skipping in muscle cells," Gene Therapy, vol. 11, pp. 131-138 (2004).

Lu et al., "Systemic delivery of antisense oligoribonucleotide restores dystrophin expression in body-wide skeletal muscles," PNAS, vol. 102(1), pp. 198-203, Jan. 4, 2005.

El-Andaloussi et al., "Induction of splice correction by cell-penetrating peptide nucleic acids.," J Gene Med, vol. 8(10), pp. 1262-1273, Oct. 2006 (Abstract).

European Patent Office, European Patent Office Action regarding European Patent Application No. EP 05 076 770.6 dated Jan. 29, 2007, 5 pages.

\* cited by examiner

After 20 minutes

31420

4694

After 24 hrs

6681

219326

SEQUENCE LISTING

<160> NUMBER OF SEQ ID NOS: 66

<210> SEQ ID NO 1
<211> LENGTH: 12
<212> TYPE: PRT
<213> ORGANISM: Artificial
<220> FEATURE:
<223> OTHER INFORMATION: Synthetic

<400> SEQUENCE: 1

Thr His Arg Pro Pro Met Trp Ser Pro Val Trp Pro
1               5                   10

<210> SEQ ID NO 2
<211> LENGTH: 7
<212> TYPE: PRT
<213> ORGANISM: Artificial
<220> FEATURE:
<223> OTHER INFORMATION: Synthetic

<400> SEQUENCE: 2

Leu Pro Trp Lys Pro Leu Gly
1               5

<210> SEQ ID NO 3
<211> LENGTH: 11
<212> TYPE: PRT
<213> ORGANISM: Artificial
<220> FEATURE:
<223> OTHER INFORMATION: Synthetic

<400> SEQUENCE: 3

His Arg Pro Pro Met Trp Ser Pro Val Trp Pro
1               5                   10

<210> SEQ ID NO 4
<211> LENGTH: 10
<212> TYPE: PRT
<213> ORGANISM: Artificial
<220> FEATURE:
<223> OTHER INFORMATION: Synthetic

<400> SEQUENCE: 4

Arg Pro Pro Met Trp Ser Pro Val Trp Pro
1               5                   10

<210> SEQ ID NO 5
<211> LENGTH: 9
<212> TYPE: PRT
<213> ORGANISM: Artificial
<220> FEATURE:
<223> OTHER INFORMATION: Synthetic

<400> SEQUENCE: 5

Pro Pro Met Trp Ser Pro Val Trp Pro
1               5

<210> SEQ ID NO 6
<211> LENGTH: 8
<212> TYPE: PRT
<213> ORGANISM: Artificial
<220> FEATURE:
<223> OTHER INFORMATION: Synthetic -continued

```
<400> SEQUENCE: 6

Pro Met Trp Ser Pro Val Trp Pro
1               5

<210> SEQ ID NO 7
<211> LENGTH: 11
<212> TYPE: PRT
<213> ORGANISM: Artificial
<220> FEATURE:
<223> OTHER INFORMATION: Synthetic

<400> SEQUENCE: 7

Thr His Arg Pro Pro Met Trp Ser Pro Val Trp
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic

<400> SEQUENCE: 8

Thr His Arg Pro Pro Met Trp Ser Pro Val
1               5                   10

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9

Thr His Arg Pro Pro Met Trp Ser Pro
1               5

<210> SEQ ID NO 10
<211> LENGTH: 8
<212> TYPE: PRT
<213> ORGANISM: Artificial
<220> FEATURE:
<223> OTHER INFORMATION: Synthetic

<400> SEQUENCE: 10

Thr His Arg Pro Pro Met Trp Ser
1               5

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

His Arg Pro Pro Met Trp Ser Pro Val Trp
1               5                   10

<210> SEQ ID NO 12
<211> LENGTH: 8
<212> TYPE: PRT
<213> ORGANISM: Artificial
<220> FEATURE:
<223> OTHER INFORMATION: Synthetic
```

```
<400> SEQUENCE: 12

Arg Pro Pro Met Trp Ser Pro Val
1               5

<210> SEQ ID NO 13
<211> LENGTH: 12
<212> TYPE: PRT
<213> ORGANISM: Artificial
<220> FEATURE:
<223> OTHER INFORMATION: Synthetic

<400> SEQUENCE: 13

Thr His Arg Pro Pro Met Trp Ser Pro Val Phe Pro
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic

<400> SEQUENCE: 14

Thr His Arg Pro Pro Met Trp Ser Pro Val Tyr Pro
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Thr His Arg Pro Pro Met Trp Ser Pro Ala Trp Pro
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic

<400> SEQUENCE: 16

Thr His Arg Pro Pro Met Trp Ser Pro Leu Trp Pro
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic

<400> SEQUENCE: 17

Thr His Arg Pro Pro Met Trp Ser Pro Ile Trp Pro
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic
```

```
<400> SEQUENCE: 18

Thr His Arg Pro Pro Met Trp Thr Pro Val Trp Pro
1               5                   10

<210> SEQ ID NO 19
<211> LENGTH: 12
<212> TYPE: PRT
<213> ORGANISM: Artificial
<220> FEATURE:
<223> OTHER INFORMATION: Synthetic

<400> SEQUENCE: 19

Thr His Arg Pro Pro Met Phe Ser Pro Val Trp Pro
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic

<400> SEQUENCE: 20

Thr His Arg Pro Pro Met Tyr Ser Pro Val Trp Pro
1               5                   10

<210> SEQ ID NO 21
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa stands for Nle (norleucine)

<400> SEQUENCE: 21

Thr His Arg Pro Pro Xaa Trp Ser Pro Val Trp Pro
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic

<400> SEQUENCE: 22

Thr His Lys Pro Pro Met Trp Ser Pro Val Trp Pro
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic

<400> SEQUENCE: 23

Ser His Arg Pro Pro Met Trp Ser Pro Val Trp Pro
1               5                   10

<210> SEQ ID NO 24
<211> LENGTH: 4
<212> TYPE: PRT
<213> ORGANISM: Artificial
```

```
<220> FEATURE:
<223> OTHER INFORMATION: Synthetic, Nuclear Localisation Signal

<400> SEQUENCE: 24

Lys Lys Lys Arg
1

<210> SEQ ID NO 25
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 25

Lys Lys Arg Lys
1

<210> SEQ ID NO 26
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 26

Lys Lys Lys Arg Lys
1               5

<210> SEQ ID NO 27
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 27

Lys Lys Arg Ser
1

<210> SEQ ID NO 28
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 28

Lys Arg Ser Lys
1

<210> SEQ ID NO 29
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 29

Lys Lys Arg Ser Lys
1               5

<210> SEQ ID NO 30
<211> LENGTH: 4
<212> TYPE: PRT
<213> ORGANISM: Artificial
<220> FEATURE:
<223> OTHER INFORMATION: Synthetic, Nuclear Localisation Sequence
```

```
<400> SEQUENCE: 30

Lys Ser Arg Lys
1

<210> SEQ ID NO 31
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 31

Ser Arg Lys Arg
1

<210> SEQ ID NO 32
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 32

Arg Lys Arg Lys
1

<210> SEQ ID NO 33
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 33

Lys Ser Arg Lys Arg
1               5

<210> SEQ ID NO 34
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 34

Ser Arg Lys Arg Lys
1               5

<210> SEQ ID NO 35
<211> LENGTH: 6
<212> TYPE: PRT
<213> ORGANISM: Artificial
<220> FEATURE:
<223> OTHER INFORMATION: Synthetic, Nuclear Localisation Signal

<400> SEQUENCE: 35

Lys Ser Arg Lys Arg Lys
1               5

<210> SEQ ID NO 36
<211> LENGTH: 7
<212> TYPE: PRT
<213> ORGANISM: Artificial
<220> FEATURE:
<223> OTHER INFORMATION: Synthetic, Nuclear Localisation Signal
```

```
<400> SEQUENCE: 36

Pro Lys Lys Lys Arg Lys Val
1               5

<210> SEQ ID NO 37
<211> LENGTH: 7
<212> TYPE: PRT
<213> ORGANISM: Artificial
<220> FEATURE:
<223> OTHER INFORMATION: Synthetic, Nuclear Localisation Signal

<400> SEQUENCE: 37

Gly Lys Lys Arg Ser Lys Val
1               5

<210> SEQ ID NO 38
<211> LENGTH: 7
<212> TYPE: PRT
<213> ORGANISM: Artificial
<220> FEATURE:
<223> OTHER INFORMATION: Synthetic, Nuclear Localisation Signal

<400> SEQUENCE: 38

Lys Ser Arg Lys Arg Lys Leu
1               5

<210> SEQ ID NO 39
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 39
gctgggcagg ccattcacac                                           20

<210> SEQ ID NO 40
<211> LENGTH: 20
<212> TYPE: DNA
<213> ORGANISM: Artificial
<220> FEATURE:
<223> OTHER INFORMATION: Antisense olignucleotide sequence

<400> SEQUENCE: 40
gctcggcagg ccgttcaccc                                           20

<210> SEQ ID NO 41
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 41
cttctcggag ctgagtgtct                                           20

<210> SEQ ID NO 42
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 42
cttctcggag ctgagcgtct                                           20
```

```
<210> SEQ ID NO 43
<211> LENGTH: 20
<212> TYPE: RNA
<213> ORGANISM: Artificial
<220> FEATURE:
<223> OTHER INFORMATION: Antisense oligonucleotide sequence

<400> SEQUENCE: 43
gcugggcagg ccauucacac                                                   20

<210> SEQ ID NO 44
<211> LENGTH: 20
<212> TYPE: RNA
<213> ORGANISM: Artificial
<220> FEATURE:
<223> OTHER INFORMATION: Antisense oligonucleotide sequence

<400> SEQUENCE: 44
gcucggcagg ccguucaccc                                                   20

<210> SEQ ID NO 45
<211> LENGTH: 20
<212> TYPE: RNA
<213> ORGANISM: Artificial
<220> FEATURE:
<223> OTHER INFORMATION: Antisense oligonucleotide sequence

<400> SEQUENCE: 45
cuucucggag cugagugucu                                                   20

<210> SEQ ID NO 46
<211> LENGTH: 20
<212> TYPE: RNA
<213> ORGANISM: Artificial
<220> FEATURE:
<223> OTHER INFORMATION: Antisense olignucleotide sequence

<400> SEQUENCE: 46
cuucucggag cugagcgucu                                                   20

<210> SEQ ID NO 47
<211> LENGTH: 21
<212> TYPE: DNA
<213> ORGANISM: Artificial
<220> FEATURE:
<223> OTHER INFORMATION: Antisense oligonucleotide sequence

<400> SEQUENCE: 47
caagaagacg gcucacucct t                                                 21

<210> SEQ ID NO 48
<211> LENGTH: 21
<212> TYPE: DNA
<213> ORGANISM: Artificial
<220> FEATURE:
<223> OTHER INFORMATION: Antisense oligonucleotide sequence

<400> SEQUENCE: 48
ttguucuucu gccgagugag g                                                 21

<210> SEQ ID NO 49
<211> LENGTH: 21
<212> TYPE: DNA
<213> ORGANISM: Artificial
<220> FEATURE:
<223> OTHER INFORMATION: Antisense oligonucleotide sequence
```

```
<400> SEQUENCE: 49
caagaaaacg gcucauucct t                                              21

<210> SEQ ID NO 50
<211> LENGTH: 21
<212> TYPE: DNA
<213> ORGANISM: Artificial
<220> FEATURE:
<223> OTHER INFORMATION: Antisense olignucleotide sequence

<400> SEQUENCE: 50
ttguucuuuu gccgaguaag g                                              21

<210> SEQ ID NO 51
<211> LENGTH: 21
<212> TYPE: DNA
<213> ORGANISM: Artificial
<220> FEATURE:
<223> OTHER INFORMATION: Antisense oligonucleotide sequence

<400> SEQUENCE: 51
gaaagccaag aagguucgat t                                              21

<210> SEQ ID NO 52
<211> LENGTH: 21
<212> TYPE: DNA
<213> ORGANISM: Artificial
<220> FEATURE:
<223> OTHER INFORMATION: Antisense oligonucleotide sequence

<400> SEQUENCE: 52
ttcuuucggu ucuuccaagc t                                              21

<210> SEQ ID NO 53
<211> LENGTH: 21
<212> TYPE: DNA
<213> ORGANISM: Artificial
<220> FEATURE:
<223> OTHER INFORMATION: Antisense oligonucleotide sequence

<400> SEQUENCE: 53
gaaggccaag aaaguucgut t                                              21

<210> SEQ ID NO 54
<211> LENGTH: 21
<212> TYPE: DNA
<213> ORGANISM: Artificial
<220> FEATURE:
<223> OTHER INFORMATION: Antisense oligonucleotide sequence

<400> SEQUENCE: 54
ttcuuccggu ucuuucaagc a                                              21

<210> SEQ ID NO 55
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 55
auucacuuuc auaaugcugg                                                20
```

```
<210> SEQ ID NO 56
<211> LENGTH: 15
<212> TYPE: DNA
<213> ORGANISM: Artificial
<220> FEATURE:
<223> OTHER INFORMATION: Antisense oligonucleotide sequence

<400> SEQUENCE: 56
tttttgattt tgtct                                                    15

<210> SEQ ID NO 57
<211> LENGTH: 15
<212> TYPE: DNA
<213> ORGANISM: Artificial
<220> FEATURE:
<223> OTHER INFORMATION: Antisense oligonucleotide sequence

<400> SEQUENCE: 57
atttaaggaa tgtga                                                    15

<210> SEQ ID NO 58
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 58
ccgtcgccct tcagcacgca                                               20

<210> SEQ ID NO 59
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 59
gtcgcccttc agcacgcaca                                               20

<210> SEQ ID NO 60
<211> LENGTH: 19
<212> TYPE: DNA
<213> ORGANISM: Artificial
<220> FEATURE:
<223> OTHER INFORMATION: Antisense oligonucleotide sequence

<400> SEQUENCE: 60
ctacagttta gcaggacag                                                19

<210> SEQ ID NO 61
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 61
tctctattgc acattccaag                                               20

<210> SEQ ID NO 62
<211> LENGTH: 20
<212> TYPE: DNA
<213> ORGANISM: Artificial
<220> FEATURE:
<223> OTHER INFORMATION: Antisense oligonucleotide sequence
```

```
<400> SEQUENCE: 62
tgatcagatc ttgaatgtga                                               20

<210> SEQ ID NO 63
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 63
gtaatcaggc ctgcaccatg                                               20

<210> SEQ ID NO 64
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 64
aagcaatcca tggactgaag                                               20

<210> SEQ ID NO 65
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 65
ctgctgctgt tgctgctgct                                               20

<210> SEQ ID NO 66
<211> LENGTH: 20
<212> TYPE: DNA
<213> ORGANISM: Artificial
<220> FEATURE:
<223> OTHER INFORMATION: Antisense oligonucleotide sequence

<400> SEQUENCE: 66
cgcctgcacc atgttcctca                                               20
```

MOLECULES FOR TARGETING COMPOUNDS TO VARIOUS SELECTED ORGANS, TISSUES OR TUMOR CELLS

RELATED APPLICATIONS

This present invention is a continuation patent application that claims priority to PCT patent application number PCT/NL2008/050470, filed Jul. 11, 2008, and European patent application No. 07112313.7, filed on Jul. 12, 1007, the entirety of which are herein incorporated by reference.

FIELD OF THE INVENTION

The present invention is in the field of in vivo targeting and provides molecules that home to, bind to and are taken up by various organs or tissues or tumor cells.

BACKGROUND OF THE INVENTION

Most therapeutic compounds are delivered to the target organ or tissue through the circulation. However, in most cases the drug or other treatment will not only target the diseased organ or tissues, but will also be taken up by other organs and tissues in the body. This can result in undesirable side effects due to, for example, generalized toxic effects throughout the patient's body. Thus, it would be desirable to selectively target specific organs or tissues, or specific types of tumor cells. In addition, coupling of a therapeutic compound to a targeting molecule can improve the uptake properties of the compound into the targeted tissue or cells, resulting in a more effective molecule. Therefore, coupling to targeting molecules yields compounds that are more effective and less toxic than the parental compound, see Curnis et al., 2000, Nature Biotechnol. 18, 1185-1190. This can be applied to a wide range of compounds, such as peptides, proteins, cytostatic agents, antibiotic and antiviral agents.

In the case of neuromuscular diseases such as myotonic dystrophy (MD) or spinal muscular atrophy (SMA) transport across the blood brain barrier and uptake into the neuronal cells is mandatory for an effective therapy. Neuron-specific peptides can be conjugated to, for example, antisense oligonucleotides (AONs) and small interfering RNA (siRNA). AONs and siRNAs have high potency to be applied as new classes of medicines for treatment of specific diseases by blocking undesired gene transcription. In the field of SMA therapy antisense-induced exon inclusion is gaining attention as a novel and promising tool for correction of the translational reading frame of the SMN2 (survival of motor neuron 2) transcript. The aim is to manipulate splicing in such a manner that the targeted exon will be included (through binding of the AONs to pre-mRNA). This would allow correction of the translational reading frame, and induction of the synthesis of a full length SMN protein.

Several reports have shown the therapeutic potential of the exon inclusion strategy for restoring full length SMN protein production (Hua et al., 2007, PLoS Biol. 5, e73; Baughan et al., 2006, Mol. Ther. 14, 54-62). However, the biggest hurdle to overcome is the poor in vivo neuronal uptake of these AONs and transport across the blood brain barrier. For other neuronal diseases, or diseases of the brain (e.g. Alzheimer, Parkinson and the like) the problem is very similar, i.e. poor in vivo uptake of the therapeutic or diagnostic compounds.

In the case of neuronal or neuro-ectodermal tumors (e.g. neuroblastoma, glioblastoma and the like), targeting is also of major importance for generating an effective therapy without side effects. Chemotherapeutic drugs can act both on normal as well as cancerous tissues, leading to this targeting requirement. For anti-sense oligonucleotide (AON-) or small interfering (si)RNA-based drugs it is known that pharmacokinetic properties are unfavourable for the free drug to reach sufficient levels at the site of the tumor, because the majority is absorbed in the liver and the kidneys. The vehicle delivering the chemotherapeutic must show sufficient half life time to effectively deliver a therapeutic agent to the desired cells, also beyond the blood brain barrier.

In light of the above, it is very clear that further improvements in delivery systems are necessary to achieve specific uptake of agents such as AONs in vivo.

SUMMARY OF THE INVENTION

It is an object of the present invention to provide compounds, preferably peptides or peptidomimetics, that home to an organ or tissue or cell type of interest, especially brain cells or neuronal cells, or by the tumor cells of neuronal or neuroectodermal origin. By coupling diagnostic moieties or moieties having a biological activity to such homing compounds, said moieties are targeted to the specific organs or tissues or cells.

After extensive research, the present inventors have identified two peptides that selectively bind to and are taken up by brain cells, neuronal cells and by tumor cells of neuronal or neuroectodermal origin. This invention thus fulfills the need of improving the in vivo uptake of for example (antisense) oligonucleotides, by conjugation of such oligonucleotides to these specific peptides. The molecules are advantageously useful in antisense therapy methods for treatment of neuromuscular disease, brain disease or tumors of neuronal or neuro-ectodermal origin, and delivery of a wide variety of diagnostics or drugs across the blood-brain barrier to brain cells, or to neuronal cells, or to tumor cells of neuronal or neuroectodermal origin.

Thus the present invention relates to a peptide or peptidomimetic comprising a sequence or consisting of a sequence selected form the group consisting of THRPPMWSPVWP (SEQ ID NO: 1) and LPWKPLG (SEQ ID NO: 2).

Also the present invention concerns conjugates of a peptide or peptidomimetics comprising a sequence or consisting of a sequence selected form the group consisting of THRPPMWSPVWP (SEQ ID NO: 1) and LPWKPLG (SEQ ID NO: 2) and a moiety selected from a biologically active moiety and diagnostic moiety linked thereto.

A conjugate as described above for use as a medicament is an aspect of this invention.

DETAILED DESCRIPTION OF THE INVENTION

Figure 1A:
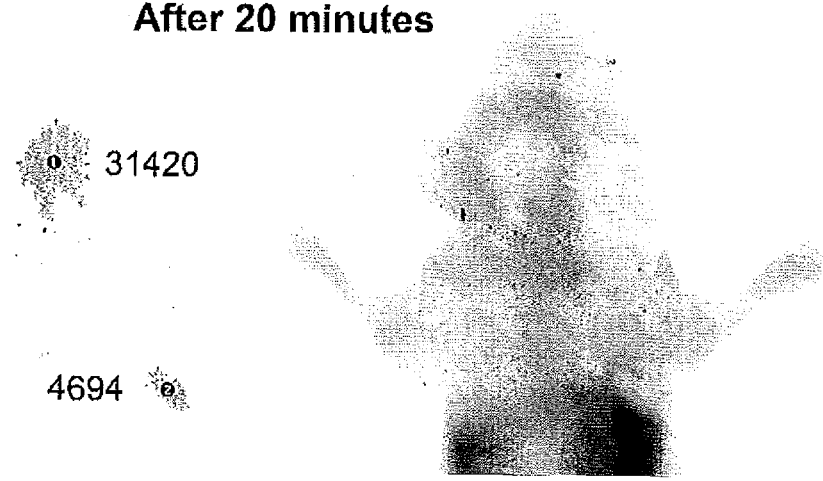
FIG. 1 (A and B) shows the uptake of labeled peptide in intravenously injected nude mice at 20 minutes (A) and 24 hours (B) after injection.

The present invention provides peptides or peptidomimetics for targeting diagnostic moieties or biologically active moieties to an organ or tissue or cell type of interest, especially across the blood brain barrier to brain cells, to neuronal cells or to tumor cells of neuronal or neuroectodermal origin.

A peptide in the context of this invention comprises at least SEQ ID NO: 1 or SEQ ID NO: 2 identified above. In one embodiment a peptide in the context of the present invention comprises a part of SEQ ID NO: 1, said part of SEQ ID NO: 1 being identical to 11, 10, 9, 8 or 7 amino acids of SEQ ID NO: 1. In one embodiment a peptide in the context of the present invention comprises or consists of SEQ ID NO: 3-12. In one embodiment a peptide in the context of the present invention comprises a variant of SEQ ID NO: 1, said variant comprising one substitution of any amino acid in SEQ ID NO: 1 with any other amino acid or derivative thereof. In one embodiment a peptide in the context of the present invention comprises or consists of SEQ ID NO: 13-23. The peptide can be fully constructed of naturally occurring L-amino acids, or can contain one or more modifications to backbone and/or side chain(s). These modifications can be introduced by incorporation of amino acid mimetics that show similarity to the natural amino acid. The group of peptides described above comprising one or more mimetics of amino acids is referred to as peptidomimetics. In the context of this invention, mimetics of amino acids include, but are not limited to, β2- and β3-amino acids, β2,2-β2,3, and β3,3-disubstituted amino acids, α,α-disubstituted amino acids, statin derivatives of amino acids, D-amino acids, α-hydroxyacids, α-aminonitriles, N-alkylamino acids and the like. In addition, the C-terminus of the peptide might be carboxylic acid or carboxamide, or other resulting from incorporation of one of the above mentioned amino acid mimetics. Furthermore, the peptides described above may contain one or more replacements of native peptide bonds with groups including, but not limited to, sulfonamide, retroamide, aminooxy-containing bond, ester, alkylketone, α,α-difluoroketone, α-fluoroketone, peptoid bond (N-allylated glycyl amide bond). Furthermore, the peptides mentioned above may contain substitutions in the amino acid side chain (referring to the side chain of the corresponding natural amino acid), for instance 4-fluorophenylalanine, 4-hydroxylysine, 3-aminoproline, 2-nitrotyrosine, N-alkylhistidine or β-branched amino acids or β-branched amino acid mimetics with chirality at the β-side chain carbon atom opposed to the natural chirality (e.g. allo-threonine, allo-isoleucine and derivatives). In one other embodiment, above mentioned group of peptides may contain close structural analogues of amino acid or amino acids mimetics, for instance ornithine instead of lysine, homophenylalanine or phenylglycine instead of phenylalanine, β-alanine instead of glycine, pyroglutamic acid instead of glutamic acid, norleucine instead of leucine or the sulfur-oxidized versions of methionine and/or cysteine. The linear and cyclized forms of the peptides mentioned above are covered by this patent, as well as their retro, inverso and/or retroinverso analogues. To those skilled in the art many more close variations may be known, but the fact that these are not mentioned here does not limit the scope of this patent. In one embodiment, a peptide or peptidomimetic according to the present invention is at most 30 amino acids in length, or at least 25 amino acids or 20 amino acids or 19, 18, 17, 16, 15, 14, 13, 12, 11, 10, 9, 8 or 7 amino acids in length.

A biologically active moiety is a compound exerting (directly or indirectly) a biological function, preferably a therapeutic function, hence is preferably a therapeutically active compound. A therapeutically active compound can be any compound known in the art and preferably is a compound that has a therapeutic effect by modulating an intercellular process. A therapeutically active compound that has a (direct) modulating effect or (direct) biological function can be for instance any protein, enzyme inhibitor, oligonucleotide, siRNA, gene, or pharmaceutical. Any biologically active compound or therapeutically active compound can be used as long as it can be linked to or can be made suitable to be linked to a peptide or peptidomimetic according to the present invention. The biologically active compound or therapeutically active compound so becomes the moiety in the compound according to the present invention. The skilled person will be able to identify suitable biologically active or therapeutically active compounds. In one embodiment the biologically active compound is a cytostatic, e.g. anti-cancer compound, such as anthracyclines (including daunorubicin, doxorubicin, epirubicin, idarubicin, mitoxantrone), alkylating agents (including cisplatin, carboplatin, oxaliplatin, chlorambucil, busulfan, melphalan, mechloethamine, cyclophosphamide, iphosphamide), anti-metabolites (including azathioprine, mercaptopurine), plant alkaloids and/or terpenoids (including vinca alkaloids and taxanes such as vincristine, vinblastine, vinorelbine, vindesine podophyllotoxin, etoposide, paclitaxel, docetaxel), tenoposide), topoisomerase inhibitors (including camphotecins irinotecan, topotecan, amsacrine), dactinomycin, dacarbazine, gemcitabine, temozolamide, mAbs (including trastuzumab, cetuximab, bevacizumab, rituximab).

In one embodiment the biologically active compound or therapeutically active compound is a compound comprising or consisting of nucleic acids or analogues thereof. Such compounds can be considered to exert (indirectly) a biological function, preferably a therapeutic function, by modulating the genetic machinery within a cell, in particular on the level of production of proteins. The nucleic acid may be a DNA, RNA or analogues thereof, such as compounds comprising 2'-O-alkyl or 2'-O-alkenyl (allyl) or 2'-O-alkynyl nucleotides, e.g. 2'-O-methyl-, 2'-O-methoxyethyl-(MOE) and 2'-O-allyl-nucleotides, locked nucleic acids (LNAs), peptide nucleic acids (PNAs), ethylene bridged nucleic acids (ENAs), phosphorothioate modified nucleotides, e.g. 2'-O-methoxyethyl phosphorothioate RNA nucleotides or 2'-O-methyl phosphorothioate RNA nucleotides, morpholino based nucleotides and combinations thereof etc. The compound comprising or consisting of nucleic acids or analogues thereof may also comprise a mixture of various nucleic acids or its analogues. It may e.g. be a chimera of a mixture of 2'O-methyl RNA and RNA, of DNA and LNA, etcetera. It may also be a gapmer, e.g. having terminal 2'O-methyl RNA nucleotides and inner DNA nucleotides. The compound may be a gene, plasmid, a polynucleotide or oligonucleotide, small interfering RNA and the like. The compound may be single stranded or double stranded.

In one embodiment a diagnostic moiety is linked to the peptides or peptidomimetics according to the present invention. The diagnostic moiety may be for in vivo or in vitro diagnostic purposes. Commonly used imaging labels, radio labels or fluorescent labels such as Cy3, Cy5, Cy5.5 and the like or green fluorescent protein (GFP) or other diagnostic proteins, possibly via recombinant expression, may be used as diagnostic moieties.

In order to prepare the conjugates according to the present invention, coupling of the biologically active moiety or diagnostic moiety to the peptides or peptidomimetics according to the present invention occurs via known methods to couple compounds to amino acids or peptides. A common method is to link a moiety to a free amino group or free hydroxyl group or free carboxylic acid group or free thiol group in a peptide or peptidomimetic. Common conjugation methods include thiol/maleimide coupling, amide or ester bond formation, or heterogeneous disulfide formation. The skilled person is well aware of standard chemistry that can be used to bring about the required coupling. The biologically active moiety or diagnostic moiety may be coupled directly to a peptide or peptidomimetic or may be coupled via a spacer or linker molecule. It is not necessary that the biologically active or diagnostic moiety is covalently linked to the peptide or peptidomimetic of the invention. It may also be conjugated via electrostatic interactions. In one embodiment the present invention also relates to a molecule comprising a peptide or peptidomimetic according to the invention and a linking part, which is not a peptide, for linking the molecule to a biologically active moiety or a diagnostic moiety. The linking part for example may be a (poly)cationic group that complexes with a biologically active poly- or oligonucleotide. Such a (poly)cationic group may be a spermine or polyethyleneimine, polyethylene glycol, poly-L-lysine and the like.

As mentioned in one embodiment the peptide or peptidomimetic according to the present invention is linked to a biologically active moiety. For example the peptide or peptidomimetic can be linked to a biologically active or therapeutic peptide and in one embodiment can even be part of the peptide or peptidomimetic basic structure. For example the amino- or carboxy-terminus of a therapeutic peptide can be extended with a sequence comprising or consisting of the peptides described above. It is to be understood that such a peptide extended with a peptide or peptidomimetic according to the invention is encompassed by a conjugate according to the present invention. The preparation of such peptides can be achieved via standard amino acid or peptide coupling procedures. In one embodiment the peptide or peptidomimetic according to the present invention is combined with a nuclear localisation signal (NLS). In one embodiment a conjugate according to the present invention is combined with a NLS. In the context of the present invention the NLS functions to direct the present conjugates, e.g. the biologically active moiety or a diagnostic moiety, into a cell nucleus, presumably via its recognition by cytosolic nuclear transport receptors. The NLS may be part of the peptide or peptidomimetic according to the present invention, e.g. the amino- or carboxy-terminus of a NLS can be extended with a sequence comprising or consisting of the peptides described above. Also a NLS may be coupled at a different position than that of the peptide or peptidomimetic according to the present invention to a biologically active moiety or a diagnostic moiety. NLS sequences are known in the art. Typically a NLS signal consists of or comprises (a few) short sequences of positively charged lysines and/or arginines, for example a NLS consist of or comprises (K)KKR(K) (SEQ ID NO: 26, (K)KRS(K) (SEQ ID NO: 29), (K)(S)RK(R)(K) (SEQ ID NO: 35). Known NLS are PKKKRKV (SEQ ID NO: 36), GKKRSKV (SEQ ID NO: 37), KSRKRKL (SEQ ID NO: 38). In one embodiment the peptide or peptidomimetic according to the present invention is combined with a NLS selected from the group consisting of SEQ ID NO: 2438.

In one embodiment a conjugate according to the invention wherein the biologically active moiety is a protein or polypeptide and wherein the peptide or peptidomimetic is comprised in the protein or polypeptide backbone is prepared by recombinant expression of the peptide or peptidomimetic together with the biologically active protein. Preferably a DNA construct is prepared such that the peptide or peptidomimetic according to the invention is expressed at a terminus of the biologically active peptide, preferably at the C-terminus of the biologically active peptide. Such preparation of DNA constructs by recombinant DNA methodology and expression in a suitable host is common practice to the skilled person.

Thus in one embodiment the present conjugate is a fusion protein of a peptide according to the present invention, e.g. a peptide of SEQ ID NO: 1 or SEQ ID NO: 2, with a therapeutically active protein, e.g. antibody, or a diagnostic (e.g. fluorescent) protein or both, optionally also comprising a NLS. Such a fusion protein can be prepared by expression of the appropriate DNA construct.

In one embodiment the present invention concerns the use of a conjugate according to present invention for the preparation of a medicament for targeting a biological active moiety or a diagnostic moiety across the blood brain barrier to brain cells, to neuronal cells or to tumor cells of neuronal or neuroectodermal origin. In one embodiment the medicament is for the treatment of a brain disorder. In one embodiment the medicament is for the treatment of a neuronal or neuromuscular disease. In one embodiment the medicament is for the treatment of a tumor of neuronal or neuroectodermal origin.

Examples of brain disorders are those involving a neurodegeneration and/or neuroinflammation event such as Stroke, Alzheimer's Disease, Parkinson's Disease and Multiple Sclerosis. Also therapy of (CNS-)disorders that benefit from neurotrophic factors, including GDNF, BDNF, EPO (erythropoietin) and anti-inflammatory antibodies (e.g. Enbrel® and Remicade®) are encompassed by the present invention. Also therapy of disorders that benefit from enzyme replacement therapies to treat the neurological component of inherited lysosomal storage diseases (Cerezyme®, Aldurazyme™, Farbrazyme®) and Pompe disease (Myozyme®) are encompassed by the present invention.

Also therapy of tumors that metastasize to the brain are encompassed by the present invention, for example those tumors that can be treated with therapeutic anti-cancer antibodies (e.g. Rituxan®, Herceptin® and Erbitux™) and anti-cancer compounds (e.g. Gleevec™ and Iressa™)

Examples of neuronal or neuromuscular diseases are myotonic dystrophy (MD) or spinal muscular atrophy (SMA), DNA repeat diseases, such as, but not limited to: coding regions repeat diseases having a polyglutamine (CAG) repeat: Huntington's disease, Haw River syndrome, Kennedy's disease/spinobulbar muscular atrophy, spino-cerebellar ataxia, or diseases having polyalanine (GCG) repeats such as: infantile spasm syndrome, deidocranial dysplasia, blepharophimosis/ptosis/epicanthus invensus syndrome, hand-foot-genital syndrome, synpolydactyl), oculopharyngeal muscular dystrophy, holoprosencephaly. Diseases with repeats in non-coding regions of genes to be treated according to the invention comprise the trinucleotide repeat disorders (mostly CTG and/or CAG repeats): myotonic dystrophy type 1, myotonic dystrophy type 2, Friedreich's ataxia, spinocerebellar ataxia, autism. Furthermore, the present conjugates can be applied for therapy of fragile site associated repeat disorder comprising various fragile X-syndromes, Jacobsen syndrome and other unstable repetitive element disorders such as myoclonus epilepsy, facioscapulohumeral dystrophy and certain forms of diabetes mellitus type 2.

Examples of tumors of neuronal or neuroectodermal origin include all neoplasms of the CNS and PNS, such as, but not limited to, neuroblastoma, medulloblastoma, glioblastoma, oligodendroglioma, oligoastrocytoma, astrocytoma, neurofibroma, ependymoma, MPNST (malignant peripheral nerve sheath tumors), ganglioneuroma or Schwannoma. Also of neuroectodermal origin are tumours such as rhabdomyosarcoma, retinoblastoma, small cell lung carcinoma, adrenal pheochromocytoma, primitive PNET (peripheral neuroectodermal tumor), Ewing's sarcoma and melanoma. In one embodiment the medicament is for the treatment of neuroblastoma, medulloblastoma, glioblastoma, oligodendroglioma, oligoastrocytoma, astrocytoma, neurofibroma, ependymoma, MPNST (malignant peripheral nerve sheath tumors), ganglioneuroma, Schwannoma, rhabdomyosarcoma, retinoblastoma, small cell lung carcinoma, adrenal pheochromocytoma, primitive PNET (peripheral neuroectodermal tumor), Ewing's sarcoma and melanoma.

In one embodiment the biologically active moiety is an oligonucleotide that is complementary to and/or capable of hybridizing to a repetitive stretch selected from the group consisting of (CAG)n, (GCG)n, (CUG)n, (CGG)n and (CCUG)n, wherein n is selected from 1-50, preferably 2-20. The integer n is selected such that in a preferred embodiment the oligonucleotide comprises at least 10 to about 50 consecutive nucleotides complementary to a repetitive element, more preferably 12 to 45 nucleotides, even more preferably 12 to 30, and most preferably 12 to 25 nucleotides complementary to a repetitive stretch.

The use of an oligonucleotide that is complementary to a polyglutamine (CAG)n tract in a transcript is particularly useful for the diagnosis, treatment and/or prevention of the human disorders Huntington's disease, several forms of spino-cerebellar ataxia or Haw River syndrome, caused by repeat expansions in the HD, HDL2/JPH3, SBMA/AR, SCA1/ATX1, SCA2/ATX2, SCA3/ATX3, SCA6/CACNAIA, SCA7, SCA17 or DRPLA human genes.

The use of an oligonucleotide that is complementary to a polyalanine (GCG)n tract in a transcript is particularly useful for the diagnosis, treatment and/or prevention of the human disorders: infantile spasm syndrome, deidocranial dysplasia, blepharophimosis, hand-foot-genital disease, synpolydactyl), oculopharyngeal muscular dystrophy and/or holoprosencephaly, which are caused by repeat expansions in the ARX, CBFA1, FOXL2, HOXA13, HOXD13, OPDM/PABP2, TCFBR1 or ZIC2 human genes.

The use of an oligonucleotide complementary to a (CUG)n repeat in a transcript is particularly useful for the diagnosis, treatment and/or prevention of the human genetic disorder myotonic dystrophy type 1, spino-cerebellar ataxia, caused by repeat expansions in the DM1/DMPK or SCA8 human genes respectively.

The use of an oligonucleotide complementary to a (CCUG)n repeat in a transcript is particularly useful for the diagnosis, treatment and/or prevention of the human genetic disorder myotonic dystrophy type 2, caused by repeat expansions in the DM2/ZNF9 gene.

The use of an oligonucleotide complementary to a (CGG)n repeat in a transcript is particularly useful for the diagnosis, treatment and/or prevention of human fragile X syndromes, caused by repeat expansion in the FRAXA/FMR1, FRAXE/FMR2 and FRAXF/FAM11A genes.

The use of an oligonucleotide complementary to a (CCG)n repeat in a transcript is particularly useful for the diagnosis, treatment and/or prevention of the human genetic disorder Jacobsen syndrome, caused by repeat expansion in the FRA11B/CBL2 gene.

In one embodiment the biologically active moiety in the peptide or peptidomimetic according to the present invention is an antisense oligonucleotide or siRNA comprising a sequence from the table below. In one embodiment the peptide or peptidomimetic conjugates according to the present invention are for the modulation of (expression of) a target gene and/or protein selected from the table 1 below and/or for therapy, in particular treatment of a disease selected from the table below.

| Antisense oligonucleotide sequence | Target gene/ protein | Disease |
|---|---|---|
| 5'-GCTGGGCAGGCCATTCACAC (SEQ ID NO: 39) | DCL | neuroectodermal tumors |
| 5'-GCTCGGCAGGCCGTTCACCC (SEQ ID NO: 40) | DCL | neuroectodermal tumors |
| 5'-CTTCTCGGAGCTGAGTGTCT (SEQ ID NO: 41) | DCL | neuroectodermal tumors |
| 5'-CTTCTCGGAGCTGAGCGTCT (SEQ ID NO: 42) | DCL | neuroectodermal tumors |
| 5'-GCUGGGCAGGCCAUUCACAC (SEQ ID NO: 43) | DCL | neuroectodermal tumors |
| 5'-GCUCGGCAGGCCGUUCACCC (SEQ ID NO: 44) | DCL | neuroectodermal tumors |
| 5'-CUUCUCGGAGCUGAGUGUCU (SEQ ID NO: 45) | DCL | neuroectodermal tumors |
| 5'-CUUCUCGGAGCUGAGCGUCU (SEQ ID NO: 46) | DCL | neuroectodermal tumors |
| 5'-CAAGAAGACGGCUCACUCCUU (SEQ ID NO: 47) | DCL | neuroectodermal tumors |
| 3'-TTGUUCUUCUGCCGAGUGAGG (SEQ ID NO: 48) | | |
| 5'-CAAGAAAACGGCUCAUUCCUU (SEQ ID NO: 49) | DCL | neuroectodermal tumors |
| 3'-TTGUUCUUUUGCCGAGUAAGG (SEQ ID NO: 50) | | |
| 5'-GAAAGCCAAGAAGGUUCGAUU (SEQ ID NO: 51) | DCL | neuroectodermal tumors |

-continued

| Antisense oligonucleotide sequence | Target gene/ protein | Disease |
|---|---|---|
| 3'-TTCUUUCGGUUCUUCCAAGCT (SEQ ID NO: 52) | | |
| 5'-GAAGGCCAAGAAAGUUCGUTT (SEQ ID NO: 53) | DCL | neuroectodermal tumors |
| 3'-TTCUUCCGGUUCUUUCAAGCA (SEQ ID NO: 54) | | |
| 5'-(CAG)n (n = 2 - 12) | DMPK | myotonic dystrophy |
| 5'-(CAG)n (n = 2 - 12) | SCA8 | Spinocerebellar ataxia 8 |
| 5'-(CCG)n (n = 2 - 12) | FMR1 | Fragile X syndrome |
| 5'-(CGG)n (n = 2 - 12) | FMR2 | Fragile XE |
| 5'-(UUC)n (n = 2 - 12) | X25 | Friedreich's ataxia |
| 5'-(CUG)n (n = 2 - 12) | AR | Spinal muscular atrophy |
| 5'-(CUG)n (n = 2 - 12) | IT15 | Huntington's disease |
| 5'-(CUG)n (n = 2 - 12) | DRPL4 | Dentatorubralpallidolusian atrophy |
| 5'-(CUG)n (n = 2 - 12) | SCA1, 2, 3, 7 | Spinocerebellar ataxia type 1, 2, 3, 7 |
| 5'-(CUG)n (n = 2 - 12) | CACNA1A | Spinocerebellar ataxia type 6 |
| 5'-(CGCG$_4$CG$_4$)n (n = 2 - 12) | CSTB | Progressive myoclonus |
| 5'-AUUCACUUUCAUAAUGCUGG (SEQ ID NO: 55) | SMN2 | Spinal muscular atrophy |
| 5'-TTTTTGATTTTGTCT (SEQ ID NO: 56) | SMN2 | Spinal muscular atrophy |
| 5'-ATTTAAGGAATGTGA (SEQ ID NO: 57) | SMN2 | Spinal muscular atrophy |
| 5'-CCGTCGCCCTTCAGCACGCA-3' (SEQ ID NO: 58) | SOD | amyotrophic lateral sclerosis (ALS) |
| 5'-GTCGCCCTTCAGCACGCACA-3' (SEQ ID NO: 59) | SOD | amyotrophic lateral sclerosis (ALS) |
| 5'-CTACAGTTTAGCAGGACAG-3' (SEQ ID NO: 60) | SOD | amyotrophic lateral sclerosis (ALS) |
| 5'-TCTCTATTGCACATTCCAAG (SEQ ID NO: 61) | Huntington (IT15) | Huntington's disease |
| 5'-TGATCAGATCTTGAATGTGA (SEQ ID NO: 62) | Huntington (IT15) | Huntington's disease |
| 5'-GTAATCAGGCCTGCACCATG (SEQ ID NO: 63) | Huntington (IT15) | Huntington's disease |
| 5'-AAGCAATCCATGGACTGAAG (SEQ ID NO: 64) | Huntington (IT15) | Huntington's disease |
| 5'-CTGCTGCTGTTGCTGCTGCT (SEQ ID NO: 65) | Huntington (IT15) | Huntington's disease |
| 5'-CGCCTGCACCATGTTCCTCA (SEQ ID NO: 66) | Huntington (IT15) | Huntington's disease |

A person skilled in the art will readily recognise that variations on the sequences in the table above are possible while retaining complementarity to the target sequence. Uracile and thymidine nucleotides are interexchangable while retaining complementarity to the target sequence. The key is that the oligonucleotide should be able to bind with sufficient efficiency to the intended target sequence. Similarly, inosine (i.e. a nucleotide containing a base able to form a wobble base pair) could replace nucleotides while retaining complementarity. In other embodiments containing (triplet) nucleotide repeat sequences, it is readily recognised that for effective binding complementarity, the oligonucleotide can start and finish with any nucleotide of the repeat sequence and the oligonucleotide does not require to be an exact multiple of the repeat sequence. As an illustrative example, (CUG)n in the table above, could also be represented amongst others by (UGC)n or (CTG)n or (CIG)n or (CUG)nCU or (CUG)n (CTG)m(CUG)p (with n, m, p being integers), etcetera.

One embodiment of the invention is the targeting of a virus or viral particle to cells. In a conjugate according to the invention the virus or viral particle is the biologically active moiety. In one embodiment the peptide or peptidomimetic according to the invention is linked to the viral biologically active moiety by including the DNA/RNA sequence of the peptide or peptidomimetic in the genome of a virus such that the peptide or peptidomimetic is expressed at the outer surface of the virus or viral particle. The recombinant methodology to bring such expression about is well known to the skilled person. The peptide or peptidomimetic thus targets the virus or viral particle to specific cells/tissue. This is of particular interest for targeted vaccination, gene therapy, gene replacement or viral exon inclusion constructs (AAV vectors expressing antisense sequences fused to either U1 or U7 small nuclear RNA; Baughan et al., 2006, Mol. Ther. 14, 54-62).

In one embodiment the peptide or peptidomimetic according to the invention is THRPPMWSPVWP (SEQ ID NO: 1). In another embodiment the peptide or peptidomimetic according to the invention is LPWKPLG (SEQ ID NO: 2).

Also encompassed by the present invention is DNA consisting of or comprising a sequence encoding a peptide according to the present invention and the complementary DNA sequence thereof and the RNA transcript of a DNA sequence consisting of or comprising a sequence encoding a peptide according to the present invention and the complementary RNA sequence thereof.

The present invention also relates to pharmaceutical compositions comprising a conjugate according to the invention and a pharmaceutically acceptable carrier.

Also it was found that the peptide THRPPMWSPVWP (SEQ ID NO: 1) can be used to monitor, in particular to identify and measure, neurite growth in neuronal or neuronally differentiated cells.

Moreover, it was found that the peptide THRPPMWSPVWP (SEQ ID NO: 1) as well as certain truncated variants thereof, in particular HRPPMWSPVWP (SEQ ID NO: 3), THRPPMWS (SEQ ID NO: 10), and BRPPMWSPVW (SEQ ID NO: 11) are selectively taken up by muscle cells, and most likely also by neuroblastoma cells. Therefore, these may be used for targeting diagnostic moieties or biologically active moieties to an organ or tissue or cell type of interest, especially to muscle cells or across the blood brain barrier to brain cells, to neuronal cells or to tumor cells of neuronal or neuroectodermal origin.

Thus, in a further aspect the invention also relates to a conjugate of a peptide or peptidomimetic comprising a sequence or consisting of a sequence selected from the group consisting of HRPPMWSPVWP (SEQ ID NO: 3), THRPPMWS (SEQ ID NO: 10) and HRPPMWSPVW (SEQ ID NO: 11) linked to a moiety selected from a biologically active moiety and diagnostic moiety.

In an embodiment, the biologically active moiety is selected from the group consisting of DNA, RNA or analogues thereof, such as compounds comprising 2'-O-alkyl, in particular 2'-O-mehoxyethyl- and 2'-O-methyl, or 2'-O-alkenyl (allyl) or 2'-O-alkynyl nucleotides, locked nucleic acids (LNAs), peptide nucleic acids (PNAs), ethylene bridged nucleic acids (ENAs), phosphorothioate modified nucleotides, morpholino based nucleotides and combinations thereof. The conjugate may be a fusion protein of a peptide of SEQ ID NO: 1, 3, 10 or 11 with a therapeutically active protein and/or a diagnostic protein. The conjugate may further comprise a nuclear localisation signal. Such conjugate may advantageously be used for the preparation of a medicament for targeting a biological active moiety or a diagnostic moiety to a muscle cell. As such, the medicament may advantageously be for the treatment of a muscle-cell associated disorder including cardiac disorders. The medicament may e.g. be for the treatment of a myopathy, muscular dystrophy or muscle wasting disease, or may be for the treatment of diabetes mellitus type II or obesity.

It is to be expected that the peptides of SEQ ID NO: 3, 10 and 11 herein referred to are also selectively taken up by neuroblastoma cells. As they are taken up specifically by both muscle cells and neuroblastoma cells, they may advantageously be used for targeting a biologically active moiety or a diagnostic moiety to neuromuscular cells for treating a neuromuscular disease. Examples of neuronal or neuromuscular diseases have been described hereinabove with reference to the peptides of SEQ ID NO: 1 and 2.

EXAMPLES

Example 1

In Vitro Uptake into Neuroblastoma and Neuronal Differentiated Cells

A selection of peptides was synthesized and provided with a fluorescent label (FAM) and screened for uptake on mouse neuroblastoma cells in vitro.

N1E-115 mouse neuroblastoma cells were incubated with the FAM-labeled peptides and photographed with an inverted fluorescence microscope, without previous fixation. As shown in the photographs, peptides LPWKPLG and THRPPMWSPVWP (SEQ ID NO: 1) were the only peptides that were efficiently taken up by the neuroblastoma cells. It was shown that the uptake results in an uniform staining of the cytoplasm as well as the nucleus of the cells.

Rat neuronal pheochromocytoma PC12 cells that were differentiated into a neuronal cell type by adding nerve growth factor (NGF) were incubated with the FAM-labeled peptide THRPPMWSPVWP (SEQ ID NO: 1) and photographed with an inverted fluorescence microscope, without previous fixation. The photographs showed uptake of the peptide into rat neuronal cells. Interestingly, in this experiment it was seen that the peptide not only stained the cytoplasm and nucleus, but also efficiently stained the NGF-induced neurite growth in these neuronally differentiated PC12 cells.

Example 2

In Vivo Targeting to Brain Cells

Peptide THRPPMWSPVWP (SEQ ID NO: 1) was labeled with a Cy5 fluorescent label and 7 nmol was injected intravenously into the tail vein of a nude mouse. Pictures were taken with a Maestro imaging system using the filters for Cy5 detection.

Figure 1B:
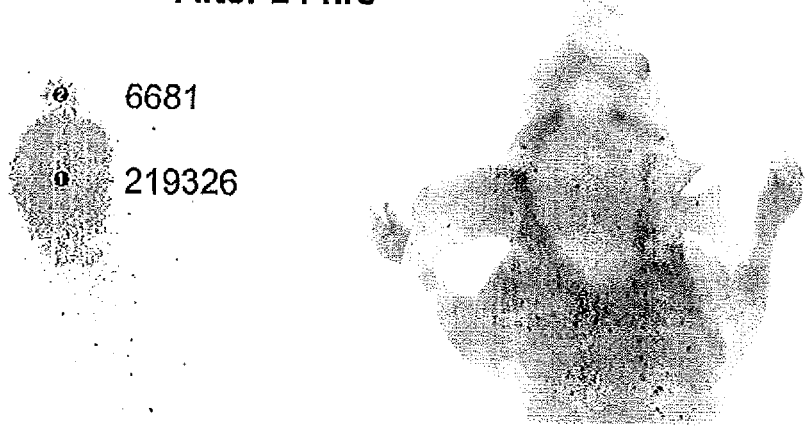

FIG. 1 shows the uptake of the peptide after 20 minutes (FIG. 1A) and after 24 hours (FIG. 1B), On the right side of FIGS. 1A and 1B, the bright light image of the mouse is combined with the detected Cy5 label shown as light blue staining. On the left side of FIGS. 1A and 1B the detected Cy5 pattern is shown separately in red for quantitation. The numbers on the left side indicate the amount of detected Cy5 label. The mouse is lying face down and a clear signal could be detected in the brain, already 20 minutes after injection. This indicates that peptide THRPPMWSPVWP (SEQ ID NO: 1) is able to cross the blood brain barrier and is subsequently taken up by the brain cells.

Example 3

Downregulation by Peptide-AON Conjugates in N115 Neuroblastoma Cells

Peptides THRPPMWSPVWP (SEQ ID NO: 1) and LPWKPLG (SEQ ID NO: 2) were conjugated to an siRNA molecule or a DNA phosphorothioate antisense oligonucleotide (AON). This siRNA and AON have been shown to be able to downregulate the DCL (doublecortin-like) gene in N115 neuroblastoma cells (unpublished observations). N115 neuroblastoma cells were incubated with the conjugates at 500 nM. After 48 hr the cells were harvested and gene silencing was detected by Western blot analysis as described (Vreugdenhil et al., 2007, Eur. J. Neurosci. 25, 635-648). In table 1 the percentage DCL downregulation of each conjugate at different concentrations is shown. All conjugates were able to induce DCL downregulation in N115 cells.

TABLE 1

DCL downregulation in N115 cells by peptide-AON conjugates at different concentrations

| AON-(conjugate) | concentration (nM) | % down-regulation |
|---|---|---|
| LPWKPLG-AON (SEQ ID NO: 2) | 500 | 62% |
| LPWKPLG-siRNA (SEQ ID NO: 2) | 500 | 99% |
| THRPPMWSPVWP-AON (SEQ ID NO: 1) | 500 | 11% |
| THRPPMWSPVWP-siRNA (SEQ ID NO: 1) | 500 | 68% |

Example 4

Uptake of Variants of THRPPMWSPVWP (SEQ ID NO: 1)

Several variants of peptide THRPPMWSPVWP (SEQ ID NO: 1) (see Table 2) were selected, synthesized with a fluorescent label and tested for uptake on KM109 cells. Peptides 3, 7, 8, 9, 10, and 11 were tested. Peptide HRPPMWSPVWP (SEQ ID NO: 3) was taken up very efficiently into the cells. Peptides THRPPMWS (SEQ ID NO: 10) and HRPPMWSPVW (SEQ ID NO: 11) were also taken up, although at a lower level. The other peptides depicted in the table below are yet to be tested for uptake on KM109 cells. Moreover, all peptides are to be tested for uptake on neuroblastoma cells in a similar fashion.

TABLE 2

Variants of THRPPMWSPVWP (SEQ ID NO: 3-23) selected for screening.

HRPPMWSPVWP (SEQ ID NO: 3)

RPPMWSPVWP (SEQ ID NO: 4)

PPMWSPVWP (SEQ ID NO: 5)

PMWSPVWP (SEQ ID NO: 6)

THRPPMWSPVW (SEQ ID NO: 7)

THRPPMWSPV (SEQ ID NO: 8)

TABLE 2-continued

Variants of THRPPMWSPVWP (SEQ ID NO: 3-23) selected for screening.

THRPPMWSP (SEQ ID NO: 9)

THRPPMWS (SEQ ID NO: 10)

HRPPMWSPVW (SEQ ID NO: 11)

RPPMWSPV (SEQ ID NO: 12)

THRPPMWSPVFP (SEQ ID NO: 13)

THRPPMWSPVYP (SEQ ID NO: 14)

THRPPMWSPAWP (SEQ ID NO: 15)

THRPPMWSPLWP (SEQ ID NO: 16)

THRPPMWSPIWP (SEQ ID NO: 17)

THRPPMWTPVWP (SEQ ID NO: 18)

THRPPMFSPVWP (SEQ ID NO: 19)

THRPPMYSPVWP (SEQ ID NO: 20)

THRPPnleWSPVWP[1] (SEQ ID NO: 21)

THKPPMWSPVWP (SEQ ID NO: 22)

SHRPPMWSPVWP (SEQ ID NO: 23)

[1]: nle = norleucine

Example 5

Uptake In Vivo of a THRPPMWSPVWP (SEQ ID NO: 1)-AON Conjugate after Systemic Delivery Peptide THRPPMWSPVWP (SEQ ID NO: 1) was conjugated to the 20-mer 2'O-methyl phosphorothioate antisense oligonucleotide (AON) M23. AON M23 alone and the THRPPMWSPVWP (SEQ ID NO: 1)-AON M23 conjugate was injected intravenously into mdx mice. The mice received 3 injections, with a 48-h interval, of 50 mg/kg of AON alone or of the conjugate and were sacrificed after 10 days. Subsequently, the level of AON M23 in the quadriceps muscle and in the heart muscle was measured with a hybridization-ligation ELISA specific for AON M23.

In table 3 the uptake of the AON M23-peptide conjugate into quadriceps and heart muscle is shown as a percentage of the uptake of AON M23 alone (AON M23 alone uptake is set at 100%). It is shown that uptake of the conjugate into quadriceps and heart muscle is 40-50% higher than with M23 AON alone.

TABLE 3

Uptake of THRPPMWSPVWP-AON conjugate into quadriceps and heart muscle after systemic delivery, relative to uptake of naked AON (set at 100%)

|  | quadriceps | heart |
|---|---|---|
| nakedAON | 100% | 100% |
| THRPPMWSPVWP-AON (SEQ ID NO: 1) | 141% | 144% |

The invention claimed is:

1. A conjugate of a peptide or peptidomimetic comprising THRPPMWSPVWP (SEQ ID NO.: 1), wherein said sequence is linked to a biologically active moiety; and
   wherein said biologically active moiety is an oligonucleotide, and
   wherein said oligonucleotide comprises a nucleotide modification selected from the group consisting of: 2'-O-methoxyethyl, 2'-O-methyl and phosphorothioate modified nucleotides.

2. The conjugate of claim 1, wherein the peptide or peptidomimetic comprises a linker which is not a peptide and which links said peptide or peptidomimetic comprising THRPPMWSPVWP (SEQ ID NO.: 1) to a biologically active moiety.

3. A conjugate of a peptide or peptidomimetic comprising a fusion protein of a peptide selected from the group consisting of: SEQ ID NO.: 1, SEQ ID NO.: 3, SEQ ID NO.: 10 and SEQ ID NO.: 11, wherein said sequence is linked to a biologically active moiety; and
   wherein said biologically active moiety is an oligonucleotide, and
   wherein said oligonucleotide comprises a nucleotide modification selected from the group consisting of: 2'-O-methoxyethyl, 2'-O-methyl and phosphorothioate modified nucleotides.

4. The conjugate according to claim 1 or 3 which further comprises a nuclear localisation signal.

5. A method of targeting a biologically active moiety across the blood brain barrier to brain cells, to neuronal cells or to tumor cells of neuronal or neuroectodermal origin of a subject using a conjugate according to claim 1 or 3 comprising the steps of:
   administering the conjugate to the subject; and
   determining the presence of the conjugate in brain cells, neuronal cells or tumor cells of neuronal or neuroectodermal origin.

6. A method of targeting a biologically active moiety to a muscle cell, using a conjugate according to claim 1 or 3 comprising the steps of:
   administering the conjugate to the subject; and
   determining the presence of the conjugate in the muscle cells.

7. A method of targeting a biologically active moiety to a muscle cell of a subject having a muscular dystrophy wherein the biologically active moiety modulates splicing of a pre-mRNA present in said cell,
  wherein said method comprises administering to the subject a conjugate according to claim 1 or 3;
  wherein said biologically active moiety modulates splicing of said targeted pre-mRNA; and wherein
  the conjugate that is administered to the subject is biologically active.

* * * * *